(12) United States Patent
Rastatter et al.

(10) Patent No.: US 9,005,107 B2
(45) Date of Patent: *Apr. 14, 2015

(54) FREQUENCY ALTERED FEEDBACK FOR TREATING NON-STUTTERING PATHOLOGIES

(75) Inventors: Michael P. Rastatter, Greenville, NC (US); Joseph S. Kalinowski, Greenville, NC (US); Andrew M. Stuart, Winterville, NC (US)

(73) Assignee: East Carolina University, Greenville, NC (US)

( * ) Notice: Subject to any disclaimer, the term of this patent is extended or adjusted under 35 U.S.C. 154(b) by 336 days.

This patent is subject to a terminal disclaimer.

(21) Appl. No.: 13/570,380

(22) Filed: Aug. 9, 2012

(65) Prior Publication Data

US 2012/0301859 A1 Nov. 29, 2012

Related U.S. Application Data

(63) Continuation of application No. 12/901,916, filed on Oct. 11, 2010, now Pat. No. 8,257,243, which is a continuation of application No. 10/530,669, filed as application No. PCT/US03/30834 on Sep. 30, 2003, now Pat. No. 7,828,712.

(60) Provisional application No. 60/417,345, filed on Oct. 9, 2002.

(51) Int. Cl.
| | | |
|---|---|---|
| *G09B 5/04* | (2006.01) | |
| *A61F 5/58* | (2006.01) | |
| *G10L 21/00* | (2013.01) | |
| *H04R 25/00* | (2006.01) | |
| *G10L 21/057* | (2013.01) | |

(52) U.S. Cl.
CPC . *A61F 5/58* (2013.01); *G10L 21/00* (2013.01); *G10L 2021/0575* (2013.01); *H04R 25/353* (2013.01); *H04R 2225/43* (2013.01)

(58) Field of Classification Search
USPC .......................... 600/25; 434/112–118, 185; 381/312–331
See application file for complete search history.

(56) References Cited

U.S. PATENT DOCUMENTS

| | | | |
|---|---|---|---|
| 4,464,119 | A | 8/1984 | Vildgrube et al. |
| 4,727,582 | A | 2/1988 | de Vries et al. |
| 4,895,519 | A | 1/1990 | Beller et al. |
| 5,133,016 | A | 7/1992 | Clark |
| D344,800 | S | 3/1994 | Lamby |

(Continued)

FOREIGN PATENT DOCUMENTS

WO    WO97/04617    2/1997

OTHER PUBLICATIONS

Armson, J. et al., *Effect of frequency altered feedback and audience size on stutterin*, European Journal of Disorders in Communication, 32, pp. 359-366, 1997.

(Continued)

*Primary Examiner* — Samuel Gilbert
(74) *Attorney, Agent, or Firm* — Myers Bigel Sibley & Sajovec, P.A.

(57) ABSTRACT

Methods and devices treat non-stuttering pathologies having impaired or decreased communication skills by administering a frequency altered auditory feedback signal to a subject having a non-stuttering pathology while the subject is speaking or talking to thereby improve the subject's communication skills.

20 Claims, 18 Drawing Sheets

(56) References Cited

U.S. PATENT DOCUMENTS

| | | | |
|---|---|---|---|
| 5,659,156 A | 8/1997 | Mauney et al. | |
| 5,765,134 A | 6/1998 | Kehoe | |
| 5,794,203 A | 8/1998 | Kehoe | |
| 5,812,659 A | 9/1998 | Mauney et al. | |
| 5,940,798 A | 8/1999 | Houde | |
| 5,961,443 A | 10/1999 | Rastatter et al. | |
| 5,995,932 A | 11/1999 | Houde | |
| 6,230,049 B1* | 5/2001 | Fischell et al. | 600/544 |
| 6,231,500 B1 | 5/2001 | Kehoe | |
| D469,081 S | 1/2003 | Perszyk et al. | |
| 6,644,973 B2* | 11/2003 | Oster | 434/178 |
| 6,745,014 B1* | 6/2004 | Seibert et al. | 455/74.1 |
| 7,828,712 B2 | 11/2010 | Rastatter et al. | |
| 2001/0007050 A1 | 7/2001 | Adelman | |

OTHER PUBLICATIONS

Armson et al., *Interpreting Results of the Fluent Speech Paradigm in Stuttering Research: Difficulties in Separating Cause From Effect*, Journal of Speech and Hearing Research, v. 37, pp. 69-82, Feb. 1994.
Black, J., *The effect of delayed side-tone upon vocal rate and intensity*, Journal of Speech and Hearing Disorders, 16, pp. 56-60, 1951.
Boller, F. et al; *Delayed Auditory Feedback and Aphasia*, Cortex 14, pp. 212-226, 1978.
Breznitz, Zvia, *Enhancing the Reading of Dyslexic Children by Reading Acceleration and Auditory Masking*, Journal of Educational Psychology, 1997, vol. 89, No. 1, pp. 105-113.
Burke, B., *Susceptibility to delayed auditory feedback and dependence on auditory or oral sensory feedback*, Journal of Communication Disorders, 8, pp. 75-96, 1975.
Chapin, C. et al, *Speech Production Mechanisms in Aphasia: A Delayed Auditory Feedback Study*; Brain and Language, 14, pp. 106-113, 1981.
Dayalu, V. et al., *Active Inhibition of Stuttering Results in Pseudofluency. A Reply to Craig*, Perceptual and Motor Skills, 94, pp. 1050-1052, 2002.
Dayalu, V. et al., *Producing the vowel/a/ prior to speaking inhibits stuttering in adults in the English language*, Neuroscience Letters 306, pp. 111-115, 2001.
Dayalu, V. et al., *Pseudofluency in Adults Who Stutter: The Illusory Outcome of Therapy*, Perceptual and Motor Skills, 94, pp. 87-96, 2002.
Dayalu, V. et al., *Stuttering Frequency on Content and Function Words in Adults Who Stutter: A Concept Revisited*, Journal of Speech, Language, and Hearing Research, vol. 45, pp. 871-878, Oct. 2002.
Dayalu, V. et al., *Stuttering therapy results in pseudofluency*, Int. J. Lang. Comm. Dis., vol. 36, Letters to Editor, No. 3, pp. 405-408, 2001.
Dobbs, R.J. et al., *Assessment of the bradyphrenia of parkinsonism: a novel use of delayed auditory feedback*, ACTA Neurol Scand 87, pp. 262-267, 1993.
Downie, A.W. et al., *Speech Disorder in Parkinsonism—Usefulness of Delayed Auditory Feedback in Selected Cases*, BJDC, vol. 16.2, pp. 135-139, 1981.
Downie, A.W. et al., *Speech disorder in Parkinsonism; use of delayed auditory feedback in selected cases*, Journal of Neurology, Neurosurgery, and Psychiatry, 44, pp. 852, 1981.
Gillis et al., *The Influence of Differential Auditory Feedback Upon the Reading of Dyslexic Children*, Neuropsychologia, 1978, vol. 16, pp. 483-489.
Hanson, W.R. et al., *DAF as Instrumental Treatment for Dysarthria in Progressive Supranuclear Palsy: A Case Report*; Journal of Speech and Hearing Disorders, pp. 268-276, May 1980.
Hargrave, S. et al., *Effect of frequency-altered feedback on stuttering frequency at normal and fast speech rates*, Journal of Speech and Hearing Research, 37, pp. 1313-1319, 1994.
Harper, L.V. et al., *Speech Self-Monitoring in Preschoolers: The Effects of Delayed Auditory Feedback on Recitation*, Perceptual and Motor Skills, 90, pp. 1157-1170, 2000.

Harris, J., *Social neuroscience, empathy, brain integration, and neurodevelopmental disorders*, Physiology & Behavior vol. 79, pp. 525-531, 2003.
Hearit Complete Auditory Tool Kit, Auditory Tools by Hearit Company, http://www.hearitllc.com/prodr.htm., (six sheets) unknown date, but for exam purposes will be deemed to be prior to Apr. 25, 2002.
Hughes, Mike, *Electronic Fluency: The Future Stuttering Solution*, Speaking Out, vol. 19, No. 3, pp. 1-25, Mar. 2002.
http://www.kayelemetrics.com, Section 10—Using Auditory Feedback in School Settings, 7 pages, © 1996-2007 KayPENTAx, printed from website on Jan. 25, 2008.
http://www.micro-dsp.com/engl/product.html#AudioPRO, Micro-Dsp Technology Co. Ltd, AudioPRO, 9 sheets, © 2002.
*Jabra FreeSpeak BT200 wireless cellphone earset (included with Pocket Fluency System)*, Pocket Fluency System™, http://www.casafuturatech.com/Catalog/pfscatalog.html, unknown date, but for exam purposes will be deemed to be prior to Apr. 25, 2002.
*Jabra Ear-Bud Cellphone earset (included with Pocket Fluency System)*, Pocket Fluency System™, http://www.casafuturatech.com/Catalog/pfscatalog.html, unknown date, but for exam purposes will be deemed to be prior to Apr. 25, 2002.
Kalinowski, J. et al., *A common element in the immediate inducement of effortless, natural-sounding, fluent speech in people who stutter: 'the second speech signal'*, Medical Hypotheses, 58(1), pp. 61-66, 2002.
Kalinowski, J. et al., *Cautionary notes on interpreting the efficacy of treatment programs for children who stutter*, Int. j. Lang. Comm. Dis., vol. 37, No. 3, pp. 359-361, 2002.
Kalinowski, J. et al., *Effects of Monitoring Condition and Frequency-Altered Feedback on Stuttering Frequency*, Journal of Speech, Language, and Hearing Research, vol. 42, pp. 1347-1354, Dec. 1999.
Kalinowski, J. et al., *Mnemonics Helpful for Physician-Patient Communication*, Family Medicine, Letters to the Editor, pp. 7-8, Jan. 2003.
Kalinowski, J. et al., *Re: Second speech signals versus prolonged speech techniques: a reply to Onslow*, Int. J. Lang. Comm. Dis., Letter to Editor, 3 sheets, 2001.
Kalinowski, J. et al., *Self-reported efficacy of an all in-the-ear-canal prosthetic device to inhibit stuttering during one hundred hours of university teaching: an autobiographical clinical commentary*, Disability and Rehabilitation, vol. 25, No. 2, pp. 107-111, 2003.
Kalinowski, J. et al., *Stutter-free and stutter-filled speech signals and their role in stuttering amelioration for English speaking adults*, Neuroscience Letters 293, pp. 115-118, 2000.
Kalinowski, J. et al., *The Efficacy of the SpeechEasy™ Protocol for Managing Stuttering: 4 Month Data. Poster Presentation at ASHS Convention*, pp. 1-15, Nov. 21, 2002.
Kalinowski, J. et al., *Inducement of fluent speech in persons who stutter via visual choral speech*, Neuroscience Letters 281, pp. 198-200, 2000.
Kalinowski, J. et al., *Choral speech: the amelioration of stuttering via imitation and the mirror neuronal system*, Neuroscience and Biobehavioral Reviews, pp. 339-347, 2003.
Kalinowski, J. et al., *Speaking with a mirror: engagement of mirror neurons via choral speech and its derivatives induces stuttering inhibition*, Medical Hypotheses 60(4), pp. 538-543, 2003.
Kershner, et al., *Modified Voice Feedback Improves Letter naming in Reading Disabled Children with Central Auditory Dysfunction*, Journal of Clinical Child Psychology, 1985, Viol. 14, No. 2, pp. 157-161.
Kohler, E. et al., *Hearing Sounds, Understanding Actions: Action Representation in Mirror Neurons*, Science vol. 297, pp. 846-848, Aug. 2002.
*Labtec Axis-002 (included with Pocket Fluency System) Pocket Fluency System™*, http://www.casafuturatech.com/Catalog/pfscatalog.html, unknown date, but for exam purposes will be deemed to be prior to Apr. 25, 2002.
Langova, J. et al., *Experimental interference with auditory feedback*, Folia Phoniatrica, 22, pp. 191-196, 1970.
Lee, B.S., *Effects of delayed speech feedback*, Journal of the Acoustical Society of America, 22, pp. 824-826, 1950.
Lee, B.S., *Artificial stutterer*, Journal of Speech and Hearing Disorders, 16, pp. 53-55, 1951.

(56) References Cited

OTHER PUBLICATIONS

Levy et al., *Fast and Slow Namers: Benefits of Segmentation and Whole Word Training* Journal of Experimental Child Psychology 73:115-138, 1999.

Lozano, R.A. et al., *Some Effects of Delayed Auditory Feedback on Dyspraxia of Speech*, Journal of Communication Disorders, 11, pp. 407-415, 1978.

McCormick, B., *Therapeutic and Diagnostic Applications of Delayed Auditory Feedback*, British Journal of Disorders of Communication, 10, pp. 98-110, 1975.

New HEARIT se, LDS Newsbriefs, vol. 37, No. 2, pp. 15, Mar./Apr. 2002.

Rastatter et al., *Quantitative Electroencephalogram of Posterior Cortical Areas of Fluent and Stuttering Participants During Reading With Normal and Altered Auditory Feedback*, Perceptual and Motor Skills, 1998, 87, pp. 623-633.

Rastatter et al. *The Effects of Frequency Altered Feedback on Reading Comprehension Abilities of Normal and Reading Disordered Children* Neuroscience Letters 416:266-271, 2007.

Rizzolatti, G. et al., *Language within our grasp*, Trends Neurosci vol. 21, No. 5, pp. 188-194, 1998.

Salame and Baddeley. *Noise, Unattended Speech and Short-Term Memory* Ergonomics 30(8):1185-1194, 1987.

Saltuklaroglu, T. et al., *Reduction of stuttering: the dual inhibition hypothesis*, Medical Hypotheses, 58(1), pp. 67-71, 2002.

Saltuklaroglu, T. et al., *Say it with me: Stuttering Inhibited*, Journal of Clinical and Experimental Neuropsychology, vol. 00, No. 0, pp. 1-8, 2003.

Saltuklaroglu, T. et al., *SpeechEasy™ Hardware, Software Installation, and Treatment Protocol Manual*, Version 3.0 Stuttering Research Group LLC, pp. 1-52, © 2002.

Saltuklaroglu, T. et al., *The end-product of behavioural stuttering therapy: three decades of denaturing the disorder*, Disability and Rehabilitation, vol. 24, No. 15, pp. 786-789, 2002.

Saltuklaroglu, T. et al., *A temporal window for the central inhibition of stuttering via exogenous speech signals in adults*, Neuroscience Letters, pp. 1-5, 2003.

Sapir et al., *Linguistic and nonlinguistic auditory processing of rapid vowel formant (F2) modulations in university students with and without developmental dyslexia*, Brain Cogn. Mar.-Apr. 2002; 48(2-3):520-6, http://www.ncbi.nlm.nih.gov/entrez/query.fcgi?cmd=Retrieve&db=PubMed&list_uids=12030500&dopt=Abstract, 1 page.

*Speaking Freely*, People, pp. 112, Sep. 16, 2002.

Stager, S.V. et al., *Modifications in Aerodynamic Variables by Persons Who Stutter Under Fluency-Evoking Conditions*, JSLHR, vol. 40, pp. 832-847 Aug. 1997.

Stager, S.V. et al., *Speech Production Changes Under Fluency-Evoking Conditions in Nonstuttering Speakers*, Journal of Speech and Hearing Research, vol. 36, pp. 245-253, Apr. 1993.

Stager, S.V. et al., *The Effects of Fluency-Evoking Conditions on Voicing Onset Types in Persons Who do and do not Stutter*, J. Commun. Disord., 31, pp. 33-52, 1998.

Stuart, A. et al., *Investigations of the Impact of Altered Auditory Feedback In-The-Ear Devices on the Speech of People Who Stutter: Initial Fitting and Four-Month Follow-up*, International Journal of Language & Communication Disorders, pp. 1-48, Date Unknown but believed to be before Oct. 2002.

Stuart, A., *Effect of delayed auditory feedback on normal speakers at two speech rates*, J. Acoust. Soc. AM. 111 (5) Pt. 1, pp. 2237-2241, May 2002.

Stuart, A. et al., *Self-Contained In-the-Ear Device to Deliver Altered Auditory Feedback: Applications for Stuttering*, Annals of Biomedical Engineering, vol. 31, pp. 233-237, 2003.

Stuart, A. et al., *Effect of monaural and binaural altered auditory feedback on stuttering frequency*, J. Accoust. Soc. Am. 101, pp. 3806-3809, Jun. 1997.

Stuart, A. et al., Abstract *Effect of DAF on Normal Speakers at normal and fast Speech Rates*, 13 pages, Date unknown but believed to be before Oct. 2002.

Tansey et al., *EMG and EEG Biofeedback Training in the Treatment of a 10-Year-Old Hyperactive Boy with a Developmental Reading Disorder*, Biofeedback and Self-Regulation, vol. 8, No. 1, 1983.

Tansey, *EEG Sensorimotor Rhythm Biofeedback Training: Some Effects on the Neurologic Precursors of Learning Disabilities*, International Journal of Psychophysiology, (1984), vol. 1, pp. 163-177.

*The Second Generation Design of SpeechEasy*, Micro-DSP Technology Co., LTD., 2 sheets, date unknown but believed to be before Oct. 2002.

Umilta, M. et al., *I know What You Are Doing: A Neurophysiological Study*, Neuron vol. 31, pp. 1-20, Jul. 2001.

Vrtunski, P.B. et al., *Response to Delayed Auditory Feedback in Patients with Hemispheric Lesions*; Cortex, 12, pp. 395-404, 1976.

Whats New With Hearit??, (2 sheets), http://www.hearitlle.com/new1.html, unknown date, but for exam purposes will be deemed to be prior to Apr. 25, 2002.

Wile and Borowsky. *What Does Rapid Automatized Naming Measure? A New RAN Task Compared to Naming and Lexical Decision* Brain and Language 90:47-62, 2004.

Williams, JHG et al., *Imitation, mirror neurons and autism*, Neuroscience and Biobehavioral Reviews 25 pp. 287-295, 2001.

Wolf and Bowers, *The Double-Deficit Hypothesis for the Developmental Dyslexias* Journal of Educational Psychology 91(3):415-438, 1999.

* cited by examiner

ITE
Full Shell

HS
Half Shell

ITC
Canal

MC
Mini Canal

CIC
Completely in Canal

FREQUENCY ALTERED FEEDBACK FOR TREATING NON-STUTTERING PATHOLOGIES

RELATED APPLICATIONS

This application is a continuation of U.S. patent application Ser. No. 12/901,916, filed Oct. 11, 2010 now U.S Pat. No. 8,257,243, which is a continuation of parent U.S. patent application Ser. No. 10/530,669, filed Sep. 21, 2005, which issued as U.S. Pat. No. 7,828,712 on Nov. 9, 2010, which is a national stage application of and claims the benefit of priority to International Application No. PCT/US2003/030834 filed Sep. 30, 2003, which claims priority to U.S. Provisional Patent Application Ser. No. 60/417,345, filed Oct. 9, 2002, the contents of which are hereby incorporated by reference as if recited in full herein.

FIELD OF THE INVENTION

The present invention relates generally to treatments for non-stuttering disorders, and may be particularly suitable for increasing reading comprehension in individuals having reading and/or learning disabilities.

BACKGROUND OF THE INVENTION

In the past, auditory masking and reading acceleration have been proposed to aid those having reading disabilities. See, e.g., Breznitz, *Enhancing the Reading of Dyslexic Children by Reading Acceleration and Auditory Masking* Jnl. Of Educational Psychology Vol. 89, No.1, pp. 103-113 (1997). In addition, Kershner et al., has proposed that a modified voice feedback during a timed naming task may improve letter-naming speed in a select sub-type of learning disabled children. Kershner et al., *Modified Voice Feedback Improves Letter Naming in Reading Disabled Children with Central Auditory Dysfunction* Jnl. of Clinical Child Psychology, Vol. 14, No. 2, pp. 157-161 (1985). Speed of letter naming has been suggested to be a good predictor of reading comprehension. DeSoto et al., *Relationship of reading achievement to verbal processing abilities*, Jnl. of Educational Psychology, 75, pp. 116-127(1983); Jansky et al., *Preventing reading failure* (NY, Harper & Row,1973). However, Kershner et al. states that frequency modification significantly improved letter recognition speed in children with central auditory dysfunction but significantly had a disruptive effect on disabled readers with intact auditory functioning, concluding that "in absolute terms, the FM effect was small" and that "[a]dditional research is needed to determine actual performance benefits of FM as a remedial intervention." Kershner et al., p. 160. More recently, researchers have reported running linguistic and non-linguistic experiments to assess whether developmental dyslexia ("DD") is related to central auditory processing deficits or to language-specific processing deficits. See, Sapir et al., *Linguistic and nonlinguistic auditory processing of rapid vowel formant (F2) modulations in university students with and without developmental dyslexia* Brain Cogn. March-April; 48 (2-3); pp. 520-526 (2002). During the non-linguistic experiment (which was run three times), the researchers had the subjects listen to synthetic vowels whose second fomant (F2) was modulated with formants F1, F3, and F4 held constant. The DD subjects' performance deteriorated over the three experimental runs, and the researchers concluded that this result suggested that resource depletion or frontal lobe dysfunction may be associated with DD. Id.

In other pathologies, delayed auditory feedback has been proposed to treat certain non-stuttering speech related disorders, such as Parkinson's disease. See, e.g., Downie et al., *Speech disorder in parkinsonism-usefulness of delayed auditory feedback in selected cases* Br. J. Disord Commun, 16(2), pp. 135-139 (September 1981). See also co-pending and co-assigned U.S. Provisional Application Ser. No. 60/375,937 the contents of which are hereby incorporated by reference as if recited in full herein.

Despite the foregoing, there remains a need for methods and related devices that can provide remedial treatments for increasing communication skills such as reading ability (cognizance, comprehension, and/or speed) for individuals having non-stuttering pathologies.

SUMMARY OF THE INVENTION

The present invention is directed to methods, systems, and devices for treating non-stuttering pathologies or disorders using frequency altered auditory feedback ("FAF").

In certain embodiments, the devices and methods can be devised to provide the FAF input using a miniaturized, minimally obtrusive device that can be worn so as to promote chronic use or therapy (upon demand where and when needed) and the like. The device may be configured to be a self-contained device or a wireless device, each with an ear mounted housing that can be sized and/or shaped as one of a behind-the-ear ("BTE"), an in-the-ear ("ITE"), in-the-canal ("ITC"), or completely-in-the-canal ("CIC") device.

In certain embodiments, the frequency alteration provided by the FAF treatment methods, systems, and devices can increase or decrease the detected auditory signal frequency in a desired amount, typically within a range of about +/−2 octaves.

The minimally obtrusive device may be configured as a compact device with an ear-supported component that is small enough to be insertable into or adjacent an ear, and, hence, supported by the ear without requiring remote wires or cabling when in operative position on/in the user.

In particular embodiments, the methods and devices can be configured to treat children with learning disabilities, including reading disabilities, in a normal educational environment such as at a school or home (outside a clinic).

The methods and devices may increase reading comprehension and/or speed in one or more of preschool-aged children, primary school-aged children, adolescents, teenagers, adults, and/or the elderly (i.e., senior citizens).

In particular embodiments, the methods and devices may be used to treat individuals having non-stuttering pathologies or disorders that impair communication skills, such as schizophrenia, autism, learning disorders such as attention deficit disorders ("ADD"), neurological impairment from brain trauma that may occur from strokes, trauma, injury, or a progressive disease such as Parkinson's disease, and the like.

In certain embodiments, the device is configured to allow treatment by ongoing substantially "on-demand" use while in position on the subject separate from and/or in addition to clinically provided episodic treatments during desired periods of service.

Certain aspects of the invention are directed toward methods for treating non-stuttering pathologies of subjects having impaired or decreased communication skills. The methods include administering a FAF signal to a subject having a non-stuttering pathology while the subject is speaking or talking to thereby improve the subject's communication skills.

In particular embodiments, the methods can include: (a) receiving an analog auditory signal of the subject at a first frequency; (b) converting the signal to a digital signal in the frequency domain; (c) altering the frequency of the digital signal within a range of about +/−2 octaves; (d) converting the signal back to the time domain and into an analog signal; (e) and then administering the frequency altered feedback signal to the user proximate in time to the receiving step.

In addition, the method can be carried out so that the step of administering the FAF signal is carried out by a device that is supported by the ear of the user and devoid of external cabling during normal operation. The administered altered auditory frequency may be shifted a desired amount within a range of about +/−2 octaves.

Other embodiments are directed to methods for treating subjects having non-stuttering pathologies or disorders presenting with an impairment or dysfunction in communication skills using FAF. The methods include: (a) positioning a (typically a self-contained or wireless) device for receiving auditory signals associated with a subject's speech in close proximity to at least one ear of an individual, the device being adapted to be in communication with at least one of the ear canals of the individual; (b) receiving in the device an audio signal associated with the subject's speech; (c) generating from the device a frequency altered auditory feedback signal having an associated frequency shift between about +/−2 octaves relative to the received audio signal; and (d) transmitting the frequency altered auditory feedback signal to at least one ear canal of the subject.

Additional aspects of the invention are directed to devices for treating non-stuttering pathologies having impaired or decreased communication skills. The devices include means for administering an FAF signal to a subject having a non-stuttering pathology while the subject is speaking or talking to thereby improve the subject's communication skills.

In particular embodiments, the devices can also include: (a) means for receiving an analog auditory signal of the subject at a first frequency; (b) means for converting the signal to a digital signal in the frequency domain; (c) means for altering the frequency of the digital signal within a range of about +/−2 octaves; (d) means for converting the signal back to the time domain and into an analog signal; and (e) means for administering the FAF signal to the user proximate in time to the receiving step. The means for administering the FAF signal may be configured as an ear supported device such as a self-contained device or a wireless compact device that has a cooperating pocket device. The ear-supported device can be devoid of external cabling during normal operation. The altered auditory frequency is shifted a desired amount within a range of about +/−2 octaves.

Other aspects include a portable device for treating non-stuttering pathologies having communication impairments, the device being supported by the ear of a user. The device includes: (a) a compact housing having opposing distal and proximal surfaces, wherein at least the proximal surface is configured for positioning in the ear canal of a user; (b) a signal processor contained within the housing; and (c) a power source operatively associated with the signal processor for supplying power thereto. The signal processor includes: (i) a receiver, the receiver generating an input signal responsive to an auditory signal associated with the user's speech; (ii) frequency altered auditory feedback circuitry operably associated with the receiver for generating a frequency altered auditory signal; and (iii) a transmitter contained within said housing and operably associated with the frequency altered auditory feedback circuitry for transmitting a frequency altered auditory signal to the user.

In particular embodiments, the signal processor is a digital programmable signal processor having externally programmable adjustable frequency shifts. These and other objects and/or aspects of the present invention are explained in detail in the specification set forth below.

DETAILED DESCRIPTION OF EMBODIMENTS OF THE INVENTION

Figure 1:
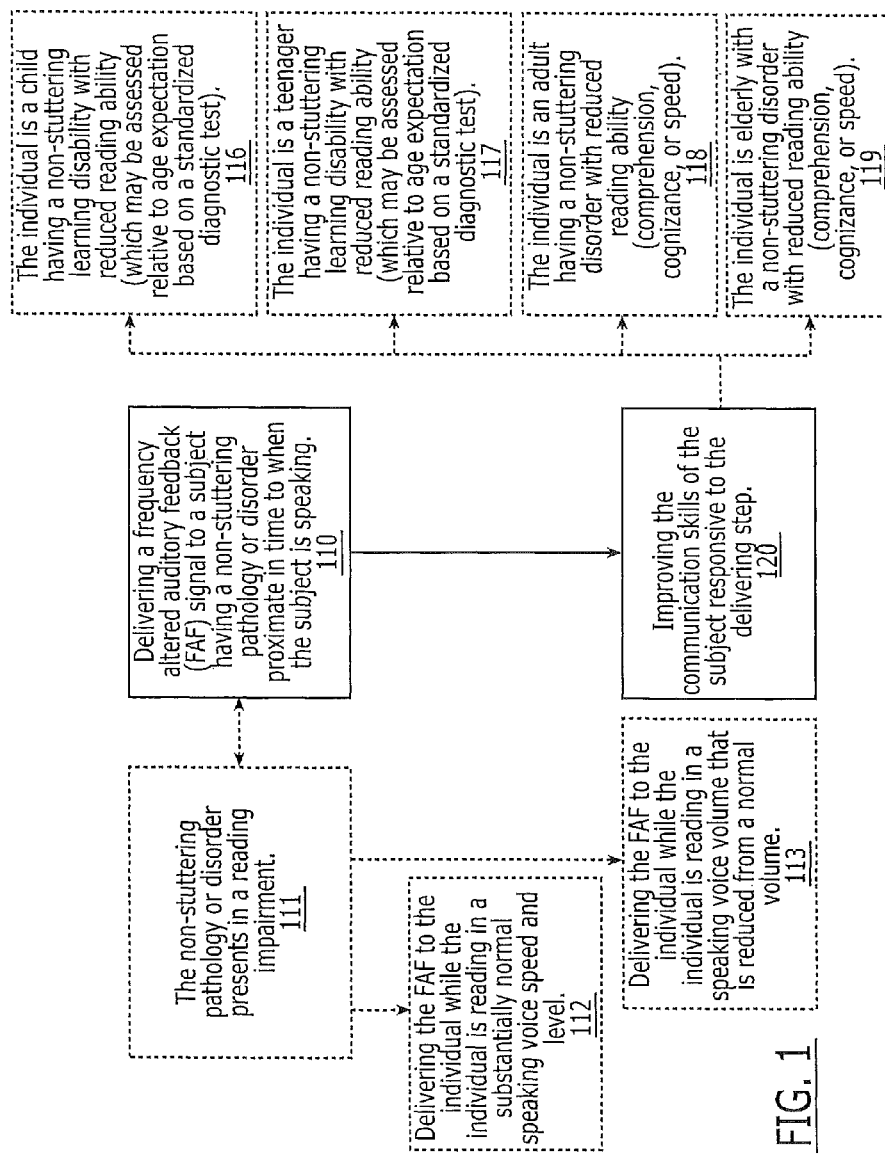
FIG. 1 is a flow diagram of operations that can be carried out to deliver an FAF input to a user having a non-stuttering disorder that can improve reading ability according to embodiments of the present invention.

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In the drawings, certain features, components, layers and/or regions may be exaggerated for clarity. Like numbers refer to like elements throughout the description of the drawings. It will be understood that when an element such as a layer, region, feature, or substrate is referred to as being "on" another element, it can be directly on the other element or indirectly on the other element such that intervening elements may also be present. In contrast, when an element is referred to as being "directly on" another element, there are no intervening elements present.

In the description of the present invention that follows, certain terms are employed to refer to the positional relationship of certain structures relative to other structures. As used herein, the term "distal" and derivatives thereof refer to a direction extending away from the ear canal (away from the center of the skull), while the term "proximal" and derivatives thereof refer to a location in the direction of the ear canal extending toward the center of the skull. In the figures, features or operations illustrated in broken line are optional unless noted otherwise.

Generally described, the present invention is directed to methods, systems, and devices that treat subjects having non-stuttering pathologies to facilitate and/or improve communication skills including reading ability and/or writing, spelling, and the like. The term "communication skills" includes, but is not limited to, writing, speech, and reading. The term "writing" is used broadly to designate assembling symbols, letters and/or words to express a thought, answer, question, or opinion and/or to generate an original or copy of a work of authorship, in a communication medium (a tangible medium of expression) whether by scribing, in print or cursive, onto a desired medium such as paper, or by writing via electronic input using a keyboard, mouse, touch screen, or voice recognition software. The term "reading ability" means reading comprehension, cognizance, and/or speed.

Referring to FIG. 1, an FAF signal is delivered to a subject having a non-stuttering pathology (disease, disorder or condition) that may subject him or her to an impairment in communication skills relative to individuals that are not afflicted with that pathology, proximate in time to when the subject is talking or speaking (block 110). The terms "talking" and "speaking" are used interchangeably herein and includes verbal expressions of voice, whether, talking, speaking, whispering, singing, yelling, and whether to others or oneself. The pathology may present with a reading impairment (block 111).

In particular embodiments, the FAF signal may be delivered while the subject is reading aloud in a substantially normal speaking voice at a normal speed and level (volume) (block 112). In other embodiments, the FAF signal may be delivered while the subject is reading aloud with a speaking voice that is reduced from a normal volume (such as a whisper or a slightly audible level). In any event, the verbal output should be sufficiently loud so that the auditory signal from the speaker's voice or speech can be detected by the device (which may be miniaturized as will be discussed below), whether the verbal output of the subject is associated with general talking, speaking, or communicating, or such talking or speaking is in relationship to spelling, reading (intermittent or choral), transforming the spoken letters into words, and/or transforming connected thoughts, words or sentences into coherent expressions or into a written work, such as in forming words or sentences for written works of authorship.

Examples of non-stuttering pathologies that may be suitable for treatment according to operations proposed by the present invention include, but are not limited to, learning disabilities ("LD"), including reading disabilities such as dyslexia, attention deficit disorders ("ADD"), attention deficit hyperactivity disorders ("ADHD") and the like, asphasis, dyspraxia, dysarthria, dysphasia, autism, schizophrenia, progressive degenerative neurological diseases such as Parkinson's disease and/or Alzheimer's disease, and/or brain injuries or impairments associated with strokes, cardiac infarctions, trauma, and the like. In certain embodiments, children having developmental praxia, auditory processing disorders, developmental language disorders or specific language impairments, or phonological processing disorders may be suitable for treatment with methods and/or devices contemplated within the scope of the present invention.

The treatment may be particularly suitable for individuals having diagnosed learning disabilities that include reading disabilities or impairments. A learning disability may be assessed by well-known testing means that establishes that an individual is performing below his/her expected level for age or I.Q. For example, a reading disability may be diagnosed by standardized tests that establish that an individual is below an age level reading expectation, such as, but not limited to, the Stanford Diagnostic Reading Test. See Carlson et al., *Stanford Diagnostic Reading Test* (NY, Harcourt Brace Javanovich, 1976). A reading disability may also be indicated by comparison to the average ability of individuals of similar age. In other embodiments, a relative decline in a subject's own reading ability may be used to establish the presence of a reading disability.

Referring again to FIG. 1, the subject to be treated may be a child having a non-stuttering learning disability with reduced reading ability relative to age expectation based on a standardized diagnostic test and the child may be of preschool age and/or primary school age (grades K-8) (block 116). In other embodiments, the individual can be a teenager or high school student (block 117), an adult (which may be a university or post-high school institution student) (block 118), or a middle age adult (ages 30-55), or an elderly person such as a senior citizen (greater than age 55, and typically greater than about age 62)(block 119). As above, the individual may have a diagnosed reading disability established by a diagnostic test, the individual may have reduced reading ability relative to the average ability of individuals of similar age, or the individual may have a recognized onset of a decrease in functionality over their own prior ability or performance.

The subject to be treated may have substantially normal hearing sensitivity, typically defined as having pure-tone thresholds at octave frequencies from 250 to 8000 Hz and speech recognition thresholds of ≤20 dB HL (American National Standards Institute, 1996). In other embodiments, the subject may have a hearing impairment.

Figure 2:
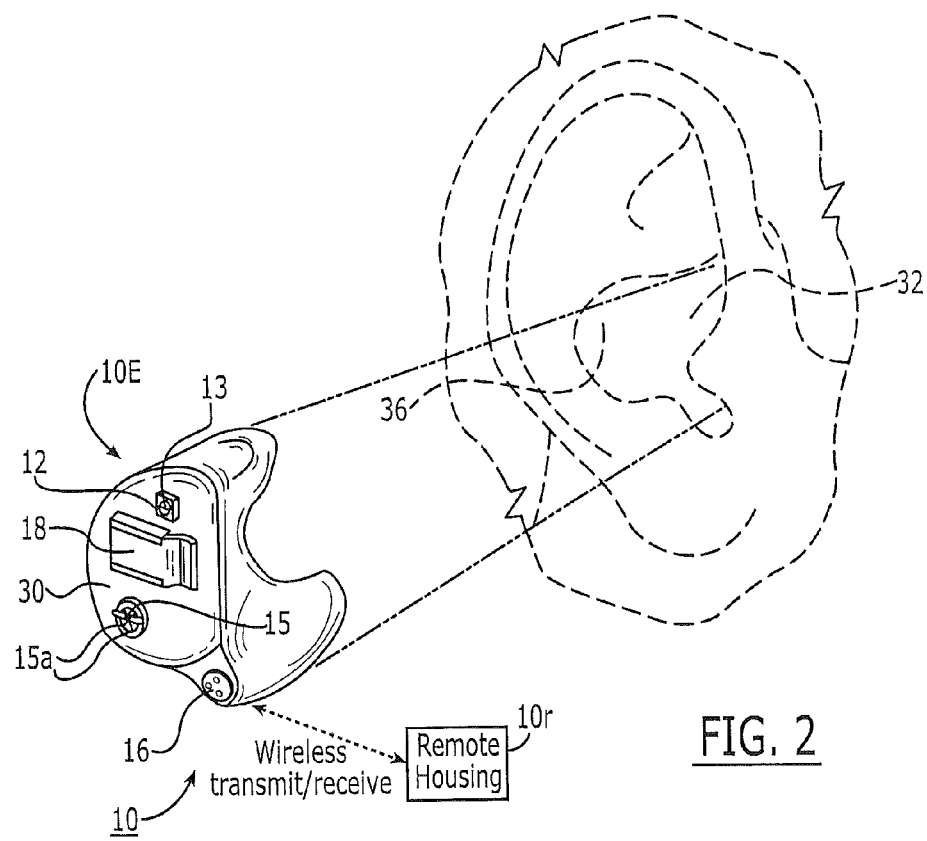
FIG. 2 is a side perspective view of a device configured for in the ear ("ITE") use for treating non-stuttering pathologies according to embodiments of the present invention.

Optionally, as shown by the features in broken line in FIG. 2, the device 10 can include a wireless portable remote component 10R (typically sized and configured to fit into a pocket or on a belt and the like) that cooperates with an ear-supported component 10E to provide the desired therapeutic input. In other embodiments, the device 10 is a self-contained ear-supported component. As is well known to those of skill in the art, the wireless system configuration may include the ear mounted component 10E, a processor which may be held in the remote housing 10H (and/or in the ear-supported housing) and a wireless transmitter that allows the processor to communicate with the ear mounted component 10E. Examples of wireless head and/or earsets include the Jabra® FreeSpeak Wireless System and other hands-free models that are available from Jabra Corporation located in San Diego, Calif. Examples of hands-free communication devices that employ ear buds, ear hooks, and the like are described in U.S. Pat. Nos. D469,081, 5,812,659 and 5,659,156, the contents of which are hereby incorporated by reference as if recited in full herein.

Alternatively, the device 10 can be self-contained and supported by the ear(s) of the user. In both the wireless and self-contained embodiments, the device 10 can be configured as a portable, compact device with the ear-mounted component being a small or miniaturized configuration. In the description of certain embodiments that follows, the device 10 is described as having certain operating components that administer the FAF. These components may reside entirely in the in the ear-mounted device 10E or certain components may be housed in the wirelessly operated remote device 10R, where such a remote device is used. For example, the controller and/or certain delayed auditory feedback signal processor circuitry and the like can be held in the remote housing 10R.

In yet other embodiments, wired versions of portable FAF feedback systems may be used, typically with a light-weight head mounted or ear-mounted component(s) (not shown).

Figure 3:
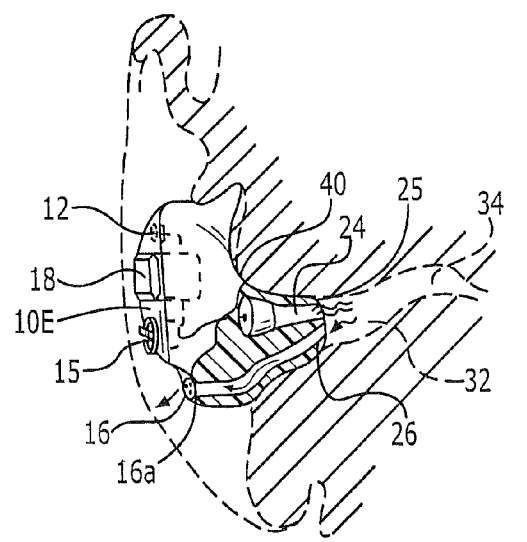
FIG. 3 is a section view of the device of FIG. 2, illustrating its position in the ear canal according to embodiments of the present invention.

In certain embodiments, as shown in FIGS. 2-5, the FAF treatment may be provided by a minimally obtrusive device 10 that is configured with an ear supported component 10E. As such, the device 10 can be configured as a portable, compact device with a small or miniaturized ear-supported housing. FIGS. 2, 3 and 5A illustrate that the device 10 and/or ear component 10E can be configured as an in-the-ear ("ITE") device. FIGS. 4A and 4B illustrate that the device 10 can include a behind-the-ear ("BTE") device. FIGS. 5B-5E illustrate various suitable configurations of ear-supported housings/devices. FIG. 5C illustrates an in-the-canal ("ITC") version, and FIG. 5B illustrates a "half-shell" ("HS") version of an ITC configuration. FIG. 5D illustrates a mini-canal version ("MC") and FIG. 5E illustrates a completely-in-the-canal ("CIC"). The CIC configuration can be described as the smallest of the ear-supported devices and is largely concealed in the ear canal.

As will be discussed in more detail below, in certain embodiments, the therapeutic device 10 for treating non-stuttering pathologies or disorders includes a small, typically miniaturized, housing which contains a power source, a signal processor including a receiver, an FAF circuit, and a transmitter therein. The housing can be configured and sized to be worn positioned proximate the ear and does not require wires or cables to external remote components during use. Certain components, such as a receiver or transducer, may be located away from the ear canal, although typically still within relatively close proximity thereto. Generally described, in operation, the portable device 10 receives input sound signals from a patient at a position in close proximity to the ear (such as via a microphone in or adjacent the ear), processes the signal, amplifies the signal, and delivers the processed signal into the ear canal of the user.

Referring now to FIG. 2, as illustrated, the ITE device 10 can be a single integrated unit that is self-contained and does not require wires and/or remote devices for operational use or may be a wireless device 10 that includes an ITE component. The device 10 includes a housing 30 of which at least a portion is configured and sized to be able to be received into the ear canal 32 and positioned close to the eardrum 34. Although shown throughout as a right ear model, a mirror image of the figure is applicable to the opposing, left ear. The housing 30 can include a proximal portion which is insertable a predetermined distance into the ear canal 32 and is sized and configured to provide a comfortable, snug fit therein. The material of the housing 30 is preferably a hard or semiflexible elastomeric material such as a polymer, copolymer, or derivative or mixture thereof.

It is also noted that although the device 10 is shown throughout as a single unit in one ear, in certain embodiments, the user may employ two discrete devices 10, with one ear-supported component in/on each ear (not shown) such that that they work in concert or independently of the other. The two ear-mounted components may be operatively in communication via a wireless communication mode or wired, such as with a thin, light-weight and minimally obtrusive cable having a length sufficient to extend between the two devices when in position in or adjacent their respective ears.

As shown in FIGS. 2 and 3, a distal portion of the device 10 can include a receiver 12, a receiver inlet 13, an accessory access door 18, a volume control 15, and a small pressure equalization vent 16. It is noted that throughout the description, the devices may employ, typically in lieu of a volume control 15, automated compression circuitry such as a wide dynamic range compression ("WDRC") circuitry. In operation, the circuitry can automatically sample incoming signals and adjust the gain of the signal to lesser and greater degrees depending on the strength of the incoming signal. The receiver 12, such as a transducer or microphone, can be disposed in a portion of the housing 30 that is positioned near the entrance to the ear canal 36 so as to receive sound waves with a minimum of blockage. More typically, the receiver 12 is disposed on or adjacent a distal exterior surface of the housing 30 and that the housing 30 optionally includes perforations 13 to allow uninhibited penetration of the auditory sound waves into the receiver or microphone.

As shown, the device 10 may also include an accessory access panel, shown in FIGS. 2 and 3 as a door member 18. The door member 18 can allow relatively easy access to the internal cavity of the device 10 so as to allow the interchange of batteries, or to repair electronics, and the like. Further, this door member 18 can also act as an "on" and "off" switch such that the device 10 can be activated or deactivated by opening and closing the door 18. The device 10 can further include a volume control that is also disposed to be accessible by a patient. As shown, the device 10 may include raised gripping projectiles 15a for easier adjustment.

The proximal side of the device 10 can hold the transmitter or speaker 24. The housing 30 can be configured to generally fill the concha of the ear 40 to prevent or block un-delayed signals from reaching the eardrum. As shown in FIG. 3, the proximal side of the housing 30 includes at least two openings 25, 26. A first opening is a vent opening 26 in fluid communication with the pressure vent 16 on the opposing side of the housing 30 As such, the vent openings 16, 26 can be employed to equalize ear canal and ambient air pressure. The distal vent opening 16 can also be configured with additional pressure adjustment means to allow manipulation of the vent opening 16 to a larger size. For example, a removable insert 16a having a smaller external aperture can be configured to be received into a larger aperture in the vent. Thus, removal of the plug results in an "adjustable" larger pressure vent opening 16.

Still referring to FIG. 3, a second opening 25 disposed so as to face into the ear canal on the proximal side of the device, is a sound bore 25 which can deliver the FAF processed signal to the inner ear canal. The opening 25 may be free of an intermediate covering(s), permitting free, substantially unimpeded delivery of the processed signal to the inner ear. Alternatively, a thin membrane, covering, or baffle (not shown) may be employed over the sound bore 25 to protect the electronics from unnecessary exposure to biological contaminants.

If desired, the housing 30 may contain a semi-flexible extension over the external wall of the ear (not shown) to further affix the housing 30 to the ear, or to provide additional structure and support, or to hold components associated with the device 10, such as power supply batteries. The operative electronic circuitry may be powered by one or more internally held power sources, such as a miniaturized battery of suitable voltage.

Figure 4A:
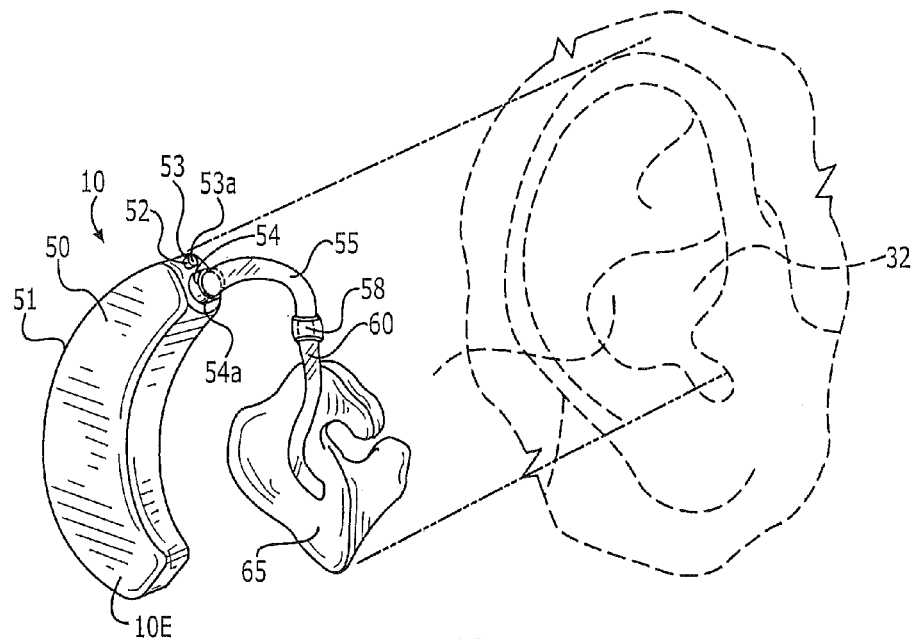
FIG. 4A is a side perspective view of a behind the ear device ("BTE") for treating non-stuttering pathologies according to alternate embodiments of the present invention.
Figure 4B:
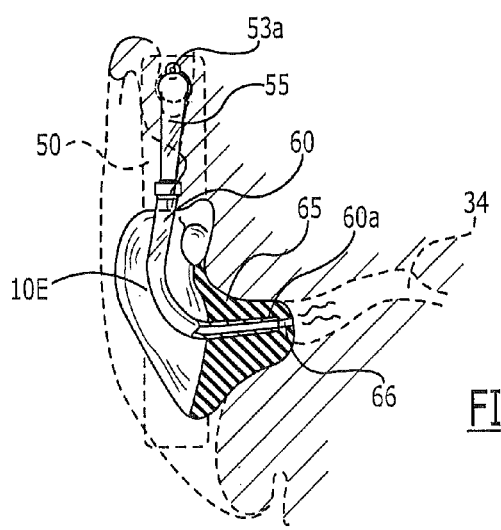
FIG. 4B is a section view of the device of FIG. 4A, illustrating the device in position, according to embodiments of the present invention.
Figure 5A:
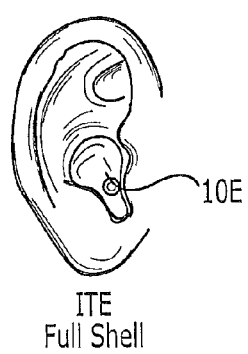
FIGS. 5A-5E are side views of examples of different types of miniaturized configurations that can be used to provide the FAF treatment for non-stuttering disorders according to embodiments of the present invention.
Figure 5B:
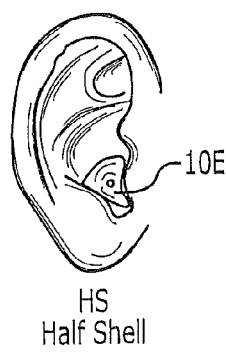
Figure 5C:
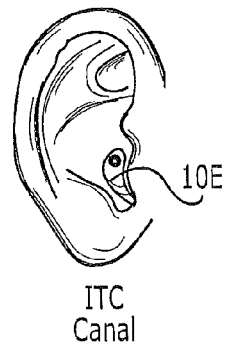
Figure 5D:
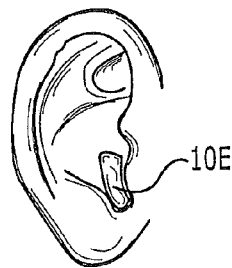
Figure 5E:
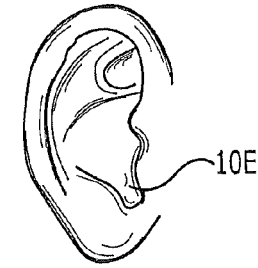

An alternative embodiment of the device 10 shown in FIGS. 2 and 3 is illustrated in FIGS. 4A and 4B with a BTE device. As illustrated, the device 10 includes a standard hearing aid type shell or housing 50, an ear hook 55, and an ear mold 65. The ear mold 65 is flexibly connected to the ear hook by mold tubing 60. The mold tubing 60 is sized to receive one end of the ear hook 58. The ear hook 55 can be formed of a stiffer material than the tubing 60. Accordingly, an end portion 58 of the ear hook 55 is inserted into the end of the mold tubing 60 to attach the components together. The opposing end portion 54 of the ear hook 55 is attached to the housing 50. The ear hook end portion 54 can be threadably engaged to a superior or top portion of the housing 50.

As shown in FIGS. 4A and 4B, the ear mold 65 is adapted for the right ear but can easily be configured for the left ear. The ear mold 65 is configured and sized to fit securely against and extend partially into the ear to structurally secure the device 10 to the ear. The tubing 60 proximal end 60a extends a major distance into the ear mold 65, and more typically extends to be slightly recessed or substantially flush with the proximal side of the ear mold 65. The tubing 60 can direct the signal and minimize the degradation of the transmitted signal along the signal path in the ear mold.

Still referring to FIGS. 4A and 4B, the proximal side of the ear mold 65 can include a sound bore 66 in communication with the tubing 60. In operation, the signal is processed in the housing 50 and is transmitted through the ear hook 54 and tubing 60 into the ear mold 65 and is delivered to the ear canal through a sound bore 66. An opening can be formed in the housing 50 to receive the auditory signal generated by the patient's speech. As shown in FIG. 4A, the opening is in communication with an opening in a receiver such as a microphone 53 positioned on the housing. The receiver or microphone 53 can be positioned in an anterior-superior location relative to the wearer and, extend out of the top of the housing 50 so as to freely intercept and receive the signals.

Corrosion-resistant materials, such as a gold collar or suitable metallic plating and/or biocompatible coating, may be included to surround the exposed component in order to protect it from environmental contaminants. The microphone opening 53a can be configured so as to be free of obstructions in order to allow the signal to enter unimpeded or freely therein.

Additionally, the housing 50 can employ various other externally accessible controls (not shown). For example, the anterior portion of the housing 51 can be configured to include a volume control (and/or compression circuitry such as WDRC, an on-off switch, and a battery door. The door can also provide access to an internal tone control and various output controls. Optionally, the BTE device can include an external port that engages an external peripheral device such as a pack for carrying a battery, where long use or increased powering periods are contemplated, or for recharging the internal power source. In addition, the device 10 may be configured with a port interface to allow interrogation or programming via an external source and may include cabling and adaptor plug-in ports to allow, same. For example, as will be discussed further below, the device 10 can be releasably attachable to an externally positioned signal processing circuitry for periodic assessment of operation, adjustment or link to an external evaluation source or clinician.

The external pack and/or remote housing 10R, when used, may be connected to the housing (not shown) and configured to be light weight and portable, and preferably supportably attached to or worn by a user, via clothing, accessories, and the like. In other embodiments the remote housing or pack may be stationary, depending on the application and desired operation.

In position, with the ear mold 65 in place, the BTE device 10 is disposed with the ear hook 55 resting on the anterior aspect of the helix of the auricle with the body of the housing 50 situated medial to the auricle adjacent to its attachment to the skull. Typically, the housing 50 is configured to follow the curve of the ear, i.e., it is a generally elongated convex. The ear-mounted housing size can vary, but is preferably sized from about 1 inch to 2.5 inches in length, measured from the highest point to the lowest point on the housing 50. The ear hook 55 is generally sized to be about 0.75 to about 1 inch for adults, and about 0.35 to about 0.5 inches for children; the length is measured with the hook 55 in the radially bent or "hook" configuration.

In certain embodiments, the receiver 53 (i.e., the microphone or transducer) is positioned within a distance of about 1 cm to 7 cm from the external acoustic meatus of the ear. It is preferable that the transducer be positioned within 4 cm of the external acoustic meatus of the ear, and more preferable that the transducer be positioned within about 2.5 cm. It is noted that the embodiments illustrated are a single, integrated housing unit that holds the power source and operational circuitry in a minimally obtrusive configuration allowing the device to be conveniently and advantageously held in use adjacent and/or in the ear.

Referring to FIGS. 5A-5E, in particular embodiments, the device 10 can include or be an ITE device (i.e., full shell, half shell, ITC, MC, or CIC device) positioned entirely within the concha of the ear and/or the ear canal. In other embodiments, as shown in FIG. 4A, the device 10 can include or be configured as a BTE device that is partially affixed over and around the outer wall of the ear so as to minimize the protrusion of the device beyond the normal extension of the helix of the ear.

Hearing aids with circuitry to enhance hearing with a housing small enough to either fit within the ear canal or be entirely sustained by the ear are well known. For example, U.S. Pat. No. 5,133,016 to Clark discloses a hearing aid with a housing containing a microphone, an amplification circuit, a speaker, and a power supply, that fits within the ear and ear canal. Likewise, U.S. Pat. No. 4,727,582 to de Vries et al. discloses a hearing aid with a housing having a microphone, an amplification circuit, a speaker, and a power supply, that is partially contained in the ear and the ear canal, and behind the ear. Each of the above-named patents are hereby incorporated by reference in their entireties as if fully recited herein. For additional description of a compact device used to ameliorate stuttering, see U.S. Pat. No. 5,961,443, the contents of which are hereby incorporated by reference as if recited in full herein.

In certain embodiments, the FAF signal is provided by digital signal processing technology that provides programmably selectable operating parameters that can be customized to the needs of a user and adjusted at desired intervals such as monthly, quarterly, annually, and the like, typically by a clinician or physician evaluating the individual. The patient fitting can be carried out with progranunably selectable and/or adjustable operating parameters such as +/−shifts in FAF (typically in about 500 Hz-200 Hz increments), linear gain control (such as about four 5-dB step size increments), independent or individually adjustable "n" band gain controls (where n can be between about 2-20 bands with center frequencies ranging from 250-7000 Hz with 20 dB gain control settings).

Further, in particular embodiments, the device 10 can be configured to selectedly provide both FAF and delayed auditory feedback ("DAF"), typically with an adjustably selectable delay time of between about 0-128 ms) and the programmable interface and the internal operating circuitry and/or the signal processor, which may be one or more of a microprocessor or nanoprocessor, can be configured to allow adjustable and/or selectable operational configurations of the device to operate in the desired feedback mode or modes. For additional description of a compact device used to ameliorate stuttering, see Stuart et al., *Self-Contained In-The Ear Device to Deliver Altered Auditory Feedback: Applications for Stuttering*, Annals of Biomedical Engr. Vol. 31, pp. 233-237 (2003), the contents of which are hereby incorporated by reference as if recited in full herein.

The FAF frequency shift or adjustment can be any desired shift, but is typically within about +/−2 octaves from the frequency of the detected auditory speech signal of the user. In certain embodiments, the frequency is adjusted at least about +/−⅛ of an octave, and typically the frequency can be adjusted at least about +/−¼ of an octave from the detected auditory signal. In particular embodiments, the frequency altered feedback signal can be adjusted so as to provide a frequency shift of at least about +/−½ of an octave, while in other embodiments, the frequency shift is at about +/−¾ to 1 octave. Other shifts, or multiples thereof, and/or different increments of octave shift, may be employed.

The frequency shift, measured in hertz, will typically be dependent upon the input signal. For example, for a 500 Hz input signal, a one octave shift is about 1000 Hz; similarly, a one octave shift of a 1000 Hz input signal is about 2000 Hz. In any event, in certain embodiments, the device be configured to be substantially "acoustically invisible" so as to provide the high fidelity of unaided listening and auditory self-monitoring while at the same time delivering optimal altered feedback, e.g, a device which can substantially maintain a relatively normal speech pattern.

The adjustment may be customized based on one or more of the particular disorder of the patient and/or the patient's response to a plurality of different "test" FAF settings during a set-up evaluation based on an improvement in readability to evaluate the efficacy of the response. In addition, the frequency adjustment may be altered over time upon periodic clinical evaluations. In other embodiments, the frequency adjustment may be set to be automatically adjusted in frequency shift increments and/or decrements at desired intervals or upon a trigger from the user.

As described above, the device 10 can be compact and portable. As such, it does not require remotely located components for normal operational use. The present invention now provides for portable and substantially non-intrusive device that allows for periodic or "chronic" use. As such, the portable device 10 can be allowed for on-going use without dedicated remote loose support hardware. The device may employ a microphone that is held proximate the ear. That is, the present invention provides a readily accessible communication enhancing (reading assist) instrument that, much like optical glasses or contacts, can be used at-will, such as only during planned or actual reading periods when there is a need for remedial intervention to promote reading ability.

Figure 6:
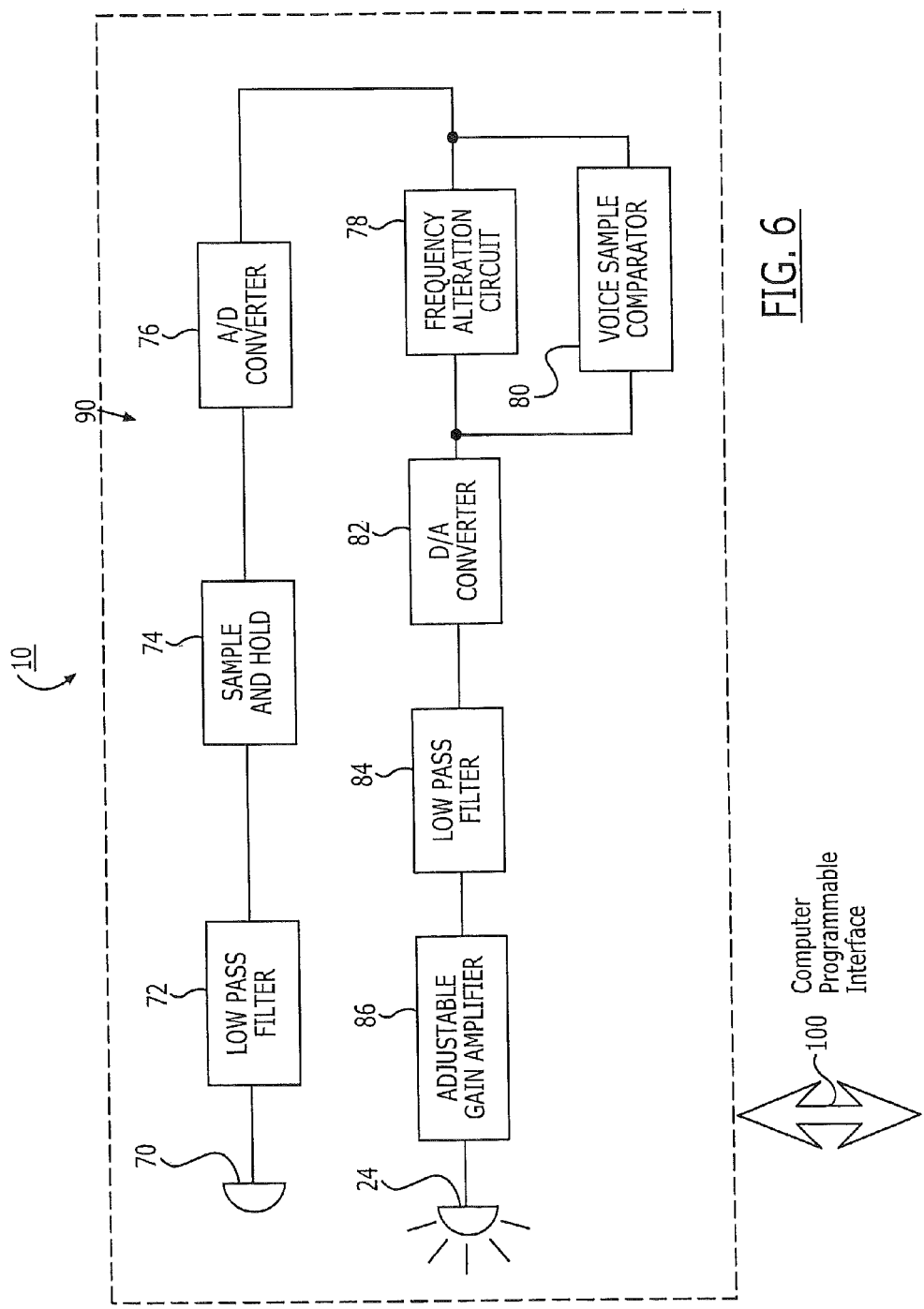
FIG. 6 is a schematic diagram of an exemplary signal processing circuit according to embodiments of the present invention.
Figure 7A:
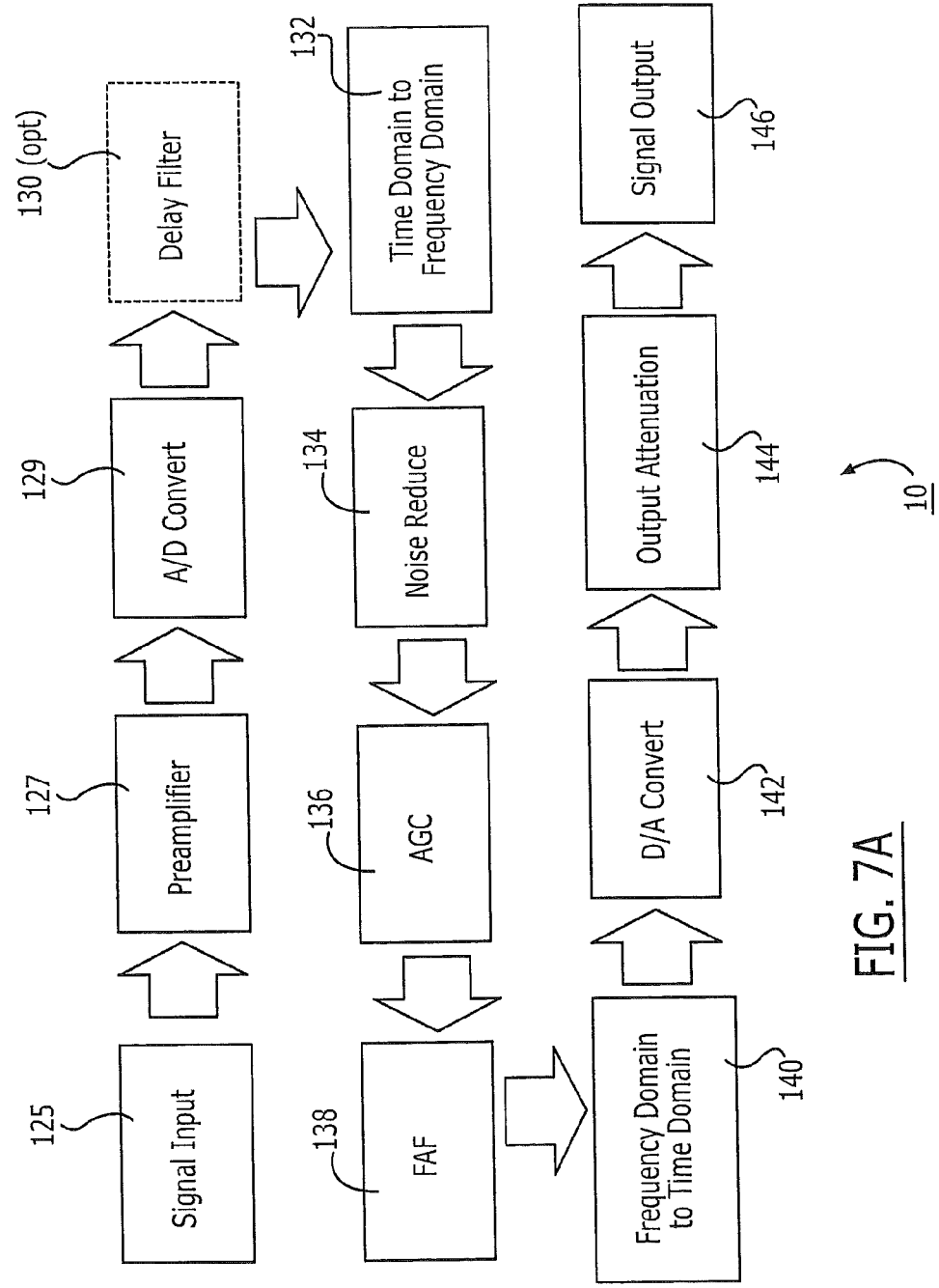
FIG. 7A is a schematic illustration of a programmable (selectable frequency shift) altered auditory feedback system for a miniaturized compact BTE, ITE, ITC, or CIC device, or the like, according to embodiments of the present invention.
Figure 7B:
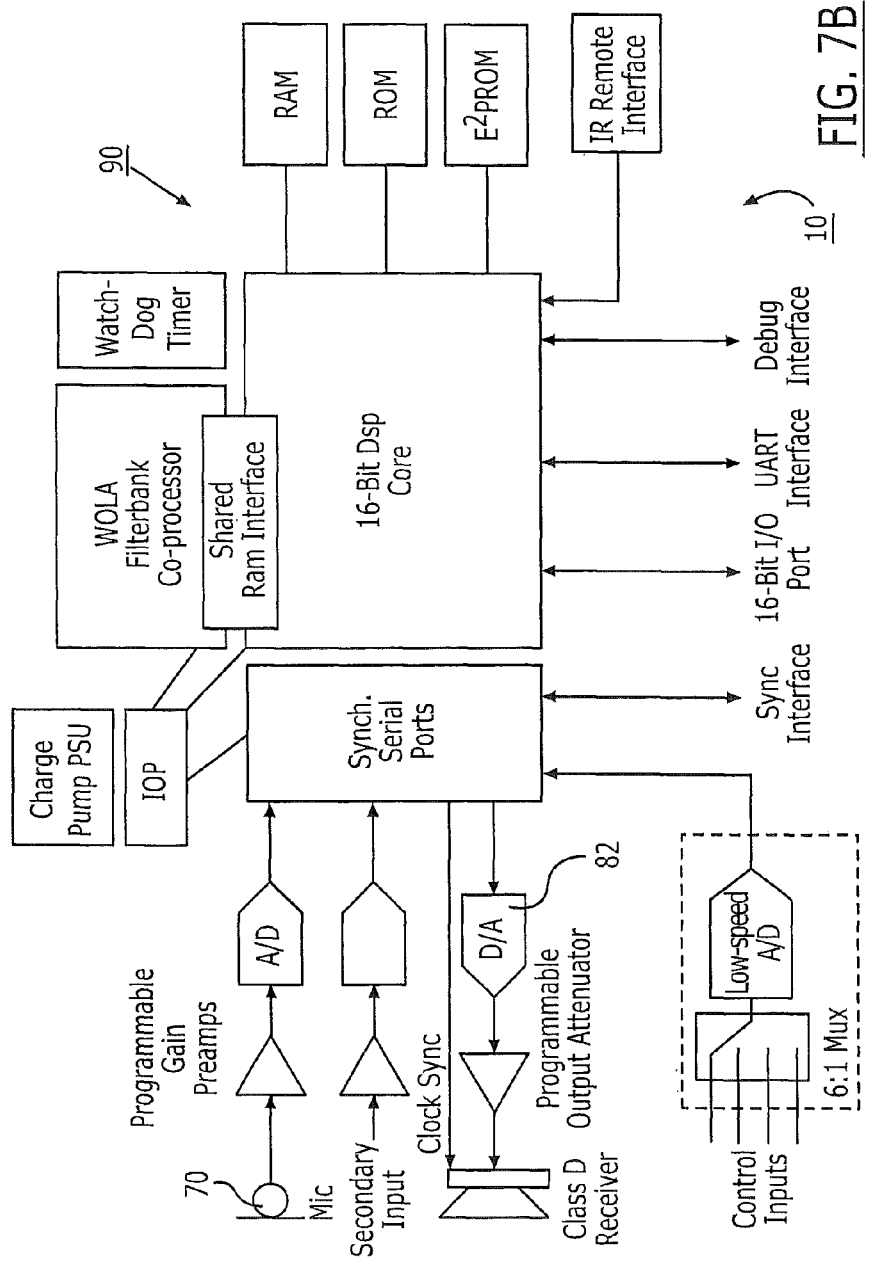
FIG. 7B is a schematic illustration of an exemplary DSP (digital signal processing) architecture that can be carried out to administer an FAF treatment to an'individual having a non-stuttering disorder according to embodiments of the present invention.

As shown in FIGS. 6, 7A, and 7B, in certain embodiments, the device 10 includes a digital signal processor (DSP) that provides at least the microphone 24, the A/D converter 76, an attenuator, and the receiver 70 can be incorporated into a digital signal processor (DSP) micro (or nano) processing chip. An exemplary miroprocessing chip is available from MICRO-DSP, a Canadian Corporation, as will be discussed further below. The DSP may be especially important in devices directed to users desiring minimally obtrusive devices that do not unduly interfere with normal life functions. Beneficially, allowing day-to-day or at-will ("on-demand") periodic use may improve reading ability (i.e., comprehension, speed and the like). Further, the compact device permits on-going or more "chronic" availability for therapeutic intervention.

FIG. 6 illustrates a schematic diagram of a device 10 having a circuit employing an exemplary signal processor 90 (DSP) with a software programmable interface 100. The broken line indicates the components may, in certain embodiments, be commonly held in or on a miniaturized device 10 such as; but not limited to, the ITC, ITE, or CIC devices described above. Generally described, the signal processor 90 receives a signal generated by a user's speech; the signal is analyzed and frequency shifted according to predetermined parameters. Finally, the FAF signal is transmitted into the ear canal of the user.

In operation, in certain embodiments, referring again to FIG. 6, the receiver 70 such as a microphone 12 or transducer (53) receives the sound waves. The receiver 70 produces an analog input signal of sound corresponding to the user's speech. According to the embodiment shown in FIG. 6, the analog input signal is converted to a stream of digital input signals. Prior to conversion to a digital signal the analog input signal is filtered by a low pass filter 72 to prevent or inhibit aliasing. The cutoff frequency for the low pass filter 72 should be sufficient to reproduce a recognizable voice sample after digitalization. A conventional cutoff frequency for voice is about 8 kHz. Filtering higher frequencies may also remove some unwanted background noise. The output of the low pass filter 72 can be input to a sample and hold circuit 74. As is well known in the art, the sampling rate should exceed twice the cutoff frequency of the low pass filter 72 to inhibit or prevent sampling errors. The sampled signals output by the sample and hold circuit 74 can be input into an Analog-to-Digital (A/D) converter 76. The digital signal stream representing each sample is then fed into a frequency shift or alteration circuit 78. The frequency shift circuit 78 could be embodied in multiple ways as is known to one of ordinary skill in the art.

Still referring to FIG. 6, the output of the frequency shift circuit 78 can then be fed into a Digital-to-Analog (D/A) converter 82. The analog signal out of the D/A converter 82 is then passed through a low pass filter 84 to accurately reproduce the FAF of the original signal. The output of the low pass filter 84 is fed into an adjustable gain amplifier 86 to allow the user (or a clinician) to adjust the output volume of the device. Finally, the amplified analog signal is connected to a speaker 24. The speaker 24 will then recreate a FAF version of the user's spoken words.

Other exemplary operations/features or components that may be used to carry out the treatments contemplated by embodiments of the present invention are illustrated in FIG. 7A. As before, an input signal is received 125, directed through a preamplifier(s) 127, then through an A/D converter 129, and optionally through a delay filter 130. The delay filter 130 may be used where DAF or combinations of FAF/DAF are desired. The digital signal can be converted from the time domain to the frequency domain 132, passed through a noise reduction circuit 134, and then through compression circuitry such as an AGC 136 or WDRC. The frequency shift is applied to the signal to provide the frequency altered feedback signal (FAF) 138, the FAF signal is reconverted to the time domain 140, passed through a D/A converter 142, and then an output attenuator 144, culminating in output of the FAF signal 146.

In operation, the illustrated operations may be programmably selected or adjusted to provide the desired output, i.e., the frequency altered auditory feedback signal. The operations shown can be carried out in and/or with a miniaturized compact BTE, ITE, ITC, or CIC device, and the like, according to embodiments of the present invention.

FIG. 7B is a schematic illustration of the architecture of a known programmable DSP 90 that may be particularly suitable for generating the FAF-based treatments, as it is particularly suitable for compact devices. This DSP architecture is known as the Toccata™ system and is available from MICRO-DSP TECHNOLOGY CO., LTD., a subsidiary of INTERNATIONAL AUDIOLOGY CENTRE OF CANADA INC. As shown, the Toccata DSP technology supports a wide-range of low-power audio applications and is believed to be the first software programmable chipset made generally available to the hearing aid industry. Generally described, with reference to FIG. 7B, by incorporating a 16-bit general-purpose DSP(RCore), a Weighted Overlap-Add (WOLA) filterbank coprocessor and a power-saving input/output controller, the Toccata™ chipset offers a practical alternative to traditional analog circuits or fixed function digital ASICs. Two 14-bit A/D and a 14-bit D/A can be used to provide high-fidelity sound. Toccata's flexible architecture makes it suitable to implement a variety of algorithms, while employing low power consumption, high fidelity, and a compact or small size. Exemplary features of the Toccata™ DSP technology include: (a) miniaturized size; (b) very low-power, about 1.5 volts or less operation; (c) low-noise, (d) 14-bit A/Ds & amp; (e) D/A interface to industry-standard microphones; (f) Class D receivers and telecoils; (g) RCore: 16-bit software-programmable Harvard architecture DSP; (h) configurable WOLA filterbank coprocessor efficiently implements analysis filtering, gain application; and (i) synthesis filtering. Exemplary performance specifications of the Tocatta™ technology DSP are described in Table 1.

TABLE 1

| Parameter | |
|---|---|
| Operation Voltage | 1.2 V |
| Current Consumption[1] | 1 mA |
| Input/Output Sampling Rate | 32 kHz |
| Frequency Response | 200-7000 Hz |
| THD + N (at −5 dB re: Digital Full Scale) | <1% |
| Programmable Analog Preamplifier Gain | 18, 22, 28 dB |
| Programmable Digital Gain | 42 dB |
| Programmable Analog Output Attenuation | 12, 18, 24, 30 dB |
| Equivalent Input Noise | 24 dB |

[1]may be algorithm dependent

In certain embodiments, the device 10 can be configured to also provide a DAF altered auditory feedback that can be activated to operate to selectively output DAF with a desired delay, typically of about 50 ms when used with the frequency alteration for non-stuttering pathologies, such as at about plus/minus one-quarter or one-half of an octave, or other desired shift as discussed hereinabove.

For the dual FAF/DAF output, the device 10 may have an adjustable delay operatively associated with the auditory delay circuit 130 (FIG. 7A). In such an embodiment, the delay circuit 130 can include a detector that detects a number of predetermined triggering events within a predetermined time envelope. Where desired, a delay circuit or wave signal processor can be placed serially in line with the FAF circuit in FIG. 6 and, as shown in FIG. 6, can include a voice sample comparator 80 for comparing a series of digitized voices samples that may be input to the delay circuit 130 and output from the delay circuit. As is known in the art, digital streams can be compared utilizing a microprocessor. The voice sample comparator 80 can output a regulating signal to the delay circuit to increase or decrease the time delay depending on the desired speech pattern, or the number of disfluencies and/or abnormal speech rate detected.

The device 10 may also have a switching circuit (not shown) to interrupt transmission from the microphone to the earphone, i.e, an activation and/or deactivation circuit. One example of this type of circuit is disclosed in U.S. Pat. No. 4,464,119 to Vildgrube et al., column 4, (see generally lines 40-59 et seq.), which is hereby incorporated herein by reference. The device 10 can be configured to be interrupted either by manually switching power off from the batteries, or by automatic switching when the user's speech and corresponding signal input falls below a predetermined threshold level. This can prevent sounds other than the user's speech from being transmitted by the device.

Alternatively, as is known in the art, other delay circuits can be employed such as, but not limited to, an analog delay circuit like a bucket-brigade circuit.

Each of the circuit components and/or operations described herein, as is known in the art, can be interchanged with other discrete or integrated circuit components to generate a suitable FAF signal as contemplated by embodiments of the present invention.

Figure 8:
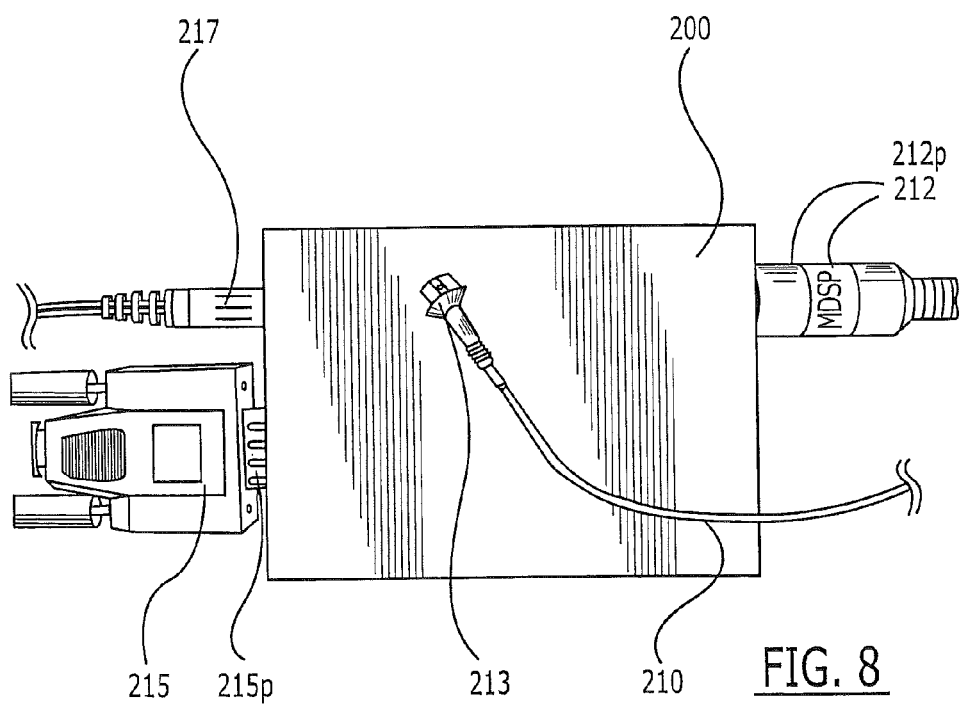
FIG. 8 is top view of a programming interface device to provide the communication between a therapeutic FAF device and a computer or processor according to embodiments of the present invention.

FIG. 8 illustrates an example of a computer interface device 200 that is used to allow communications between a computer (not shown) via a cable 215 extending from a serial (COM) port 215*p* on the interface device 200 to the compact treatment device 10 via a cable 210. The cable 210 is connected to the interface device 200 at port 212*p*. The other end 213 of the cable 210 is configured to connect to one or more configurations of the compact therapeutic device 10. The interface device 200 also includes a power input 217. One commercially available programming interface instrument is the AudioPRO from Micro-DSP Technology, LTD, having a serial RS-232C cable that connects to a computer port and a CS44 programming cable that releaseably connects to the FAF treatment device 10. See URL www.micro-dsp.com/product.htm.

Figure 9:
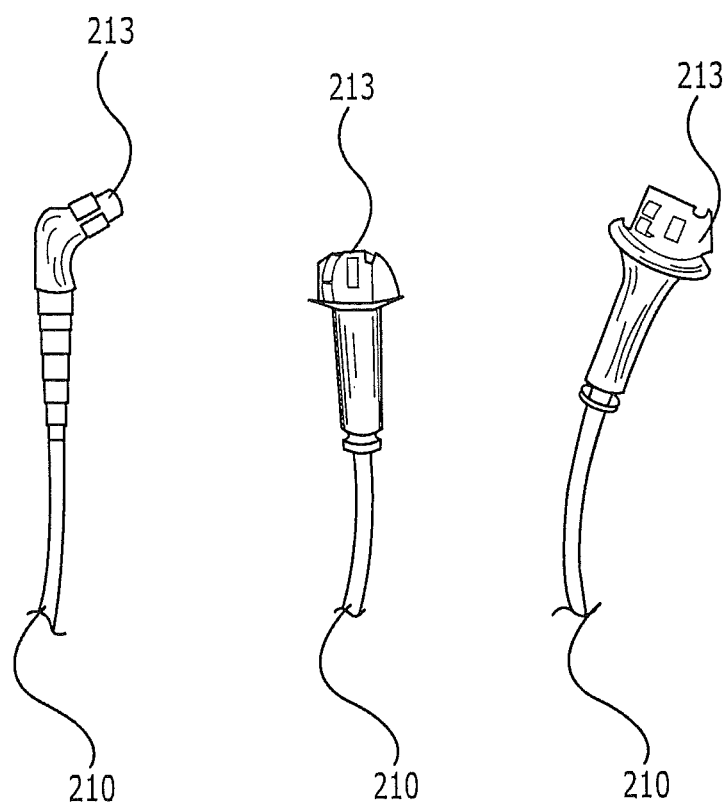
FIG. 9 is an enlarged top view of the treatment device-end portion of an interface cable configured to connect the device to a programmable interface according to embodiments of the present invention.
Figure 10:
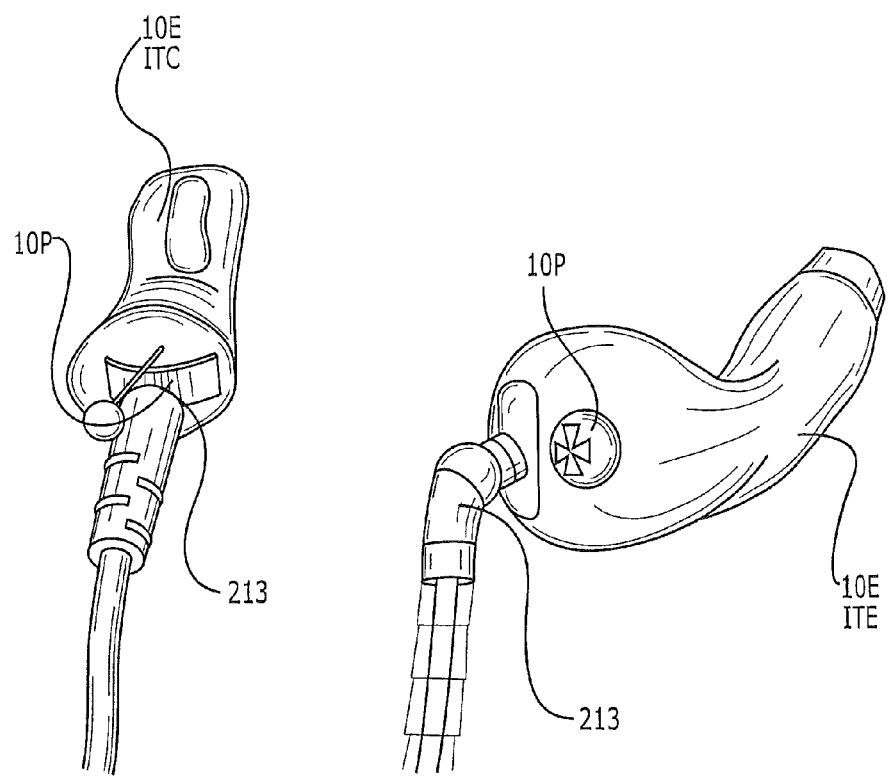
FIG. 10 is an enlarged top view of the interface cable shown in FIGS. 8 and 9 illustrating the connection to two exemplary devices.
Figure 11:
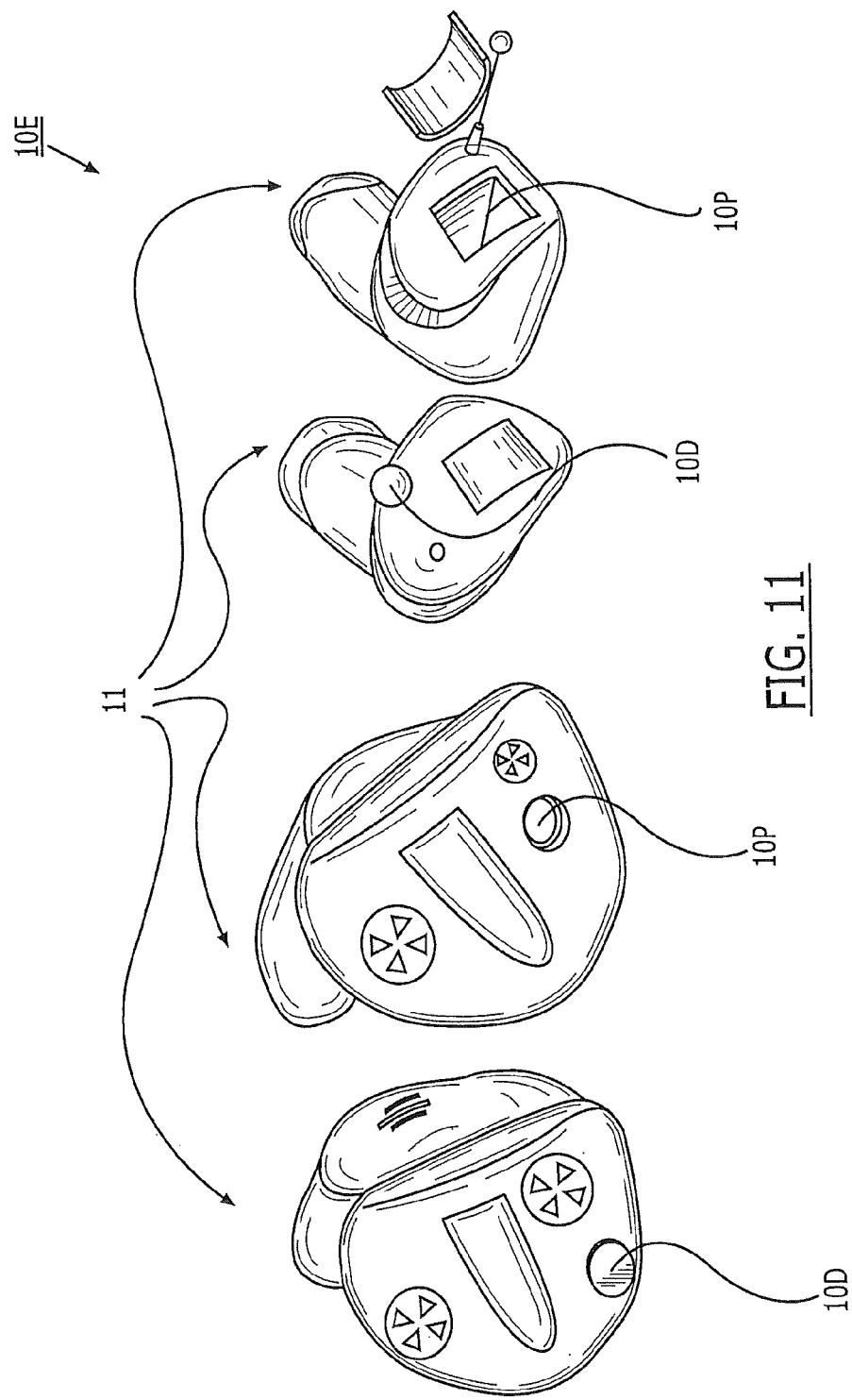
FIG. 11 is a top perspective view of multiple differently sized compact devices, each of the devices having computer interface access ports according to embodiments of the present invention.

FIG. 9 illustrates an enlarged view of a portion of the cable 210. The end shown 213 connects directly into a respective compact therapeutic device 10 as shown in FIGS. 10 and 11. FIG. 11 illustrates that an access port 10p, typically accessible by opening an externally releasable door 10D, (that may be the battery door) is used to connect the interface cable 210 to the digital signal processor 90. FIG. 10 illustrates two greatly enlarged devices 10E with the cable end connection 213 attached, each of which may have a respective door 10d over the port 10p. The device 10 shown on the left side of FIG. 10 includes or is an ITC device while that shown on the right side includes or is an ITE device. Each has a cable end connection 213 that is modified to connect to the ear-device 10E. The ITC device connection 213 includes slender elongated portion to enter into the core of the ITC device.

Figure 12:
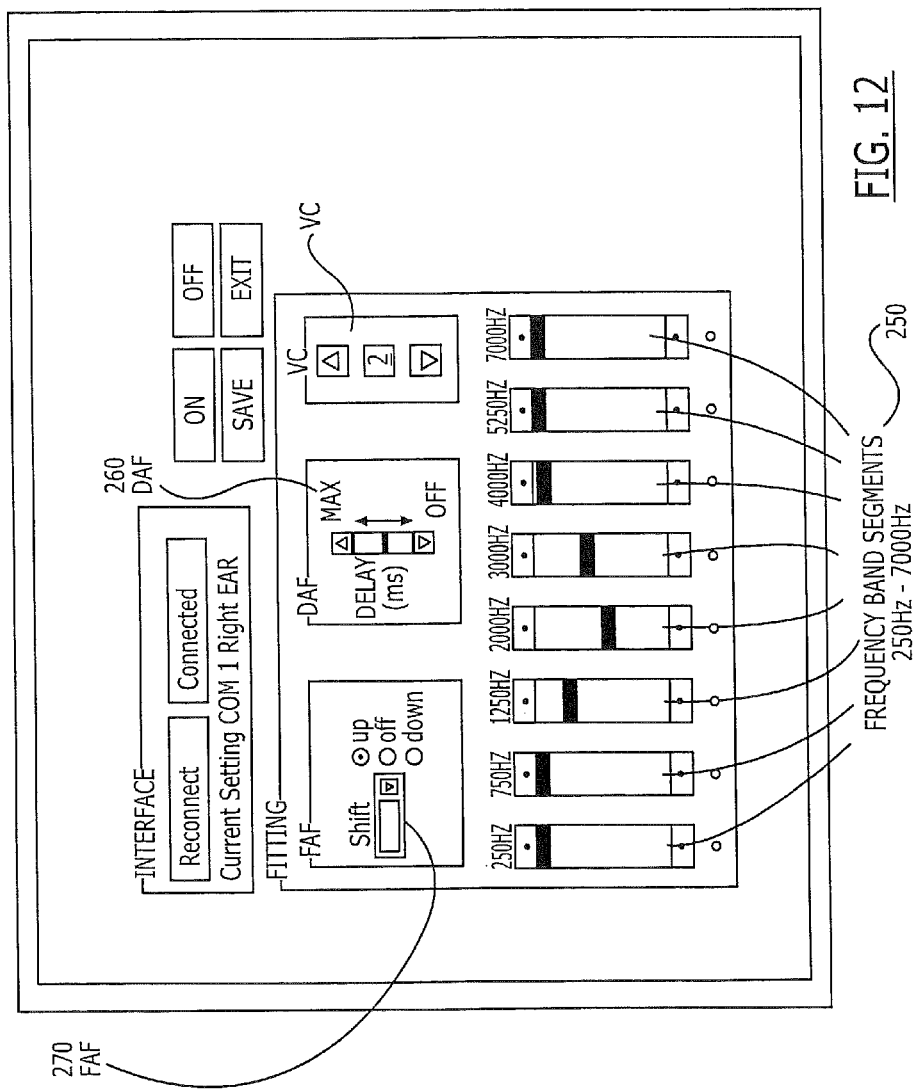
FIG. 12 is a screen view of a programmable input program providing a clinician selectable program parameters according to embodiments of the present invention.

FIG. 12 illustrates a user display input interface used to adjust or select the programmable features of the device 10 to fit or customize to a particular user or condition. The overall gain can be adjusted as well as the gain for each "n" band gain control with associated center frequencies 250 (i.e., where n=eight, each of the eight bands can be respectively centered at a corresponding one of 250 Hz, 750 Hz, 1250 Hz, 2000 Hz, 3000 Hz, 4000 Hz, 5250 Hz, 7000 Hz). Typically, n can be between about 2-20 different bands with spaced apart selected center frequencies. For DAF implementations, the delay can be adjusted by user/programmer or clinician set-up selection 260 in millisecond increments and decrements (to a maximum) and can be turned off as well. The FAF is adjustable via user input 270 by clicking and selecting the frequency desired. The frequency adjustment can be adjustable by desired hertz increments and decrements and may be shifted up, down, and turned off. Octave adjustments may alternately be generated and selectable.

As will be appreciated by those of skill in the art, the digital signal processor and other electronic components as described above may be provided by hardware, software, or a combination of the above. Thus, while the various components have been described as discrete elements, they may in practice be implemented by a microprocessor or microcontroller including input and output ports running software code, by custom or hybrid chips, by discrete components or by a combination of the above. For example, one or more of the A/D converter 76, the delay circuit 78, the voice sample comparator 80, and the gain 86 can be implemented as a programmable digital signal processor device. Of course, the discrete circuit components can also be mounted separately or integrated into a printed circuit board as is known by those of skill in the art. See generally Wayne J. Staab, *Digital Hearing Instruments,* 38 Hearing Instruments No. 11, pp. 18-26 (1987).

In any event, the electroacoustic operating parameters of the device preferably include individually adjustable and controllable power output, gain, and frequency response components with suitable electroacoustic response. Fixed circuits may also be employed with fixed maximum output, gain, and frequency response while also providing an adjustable volume control for the wearer. In operation, the device will preferably operate with "low" maximum power output, "mild" gain, and a relatively "wide" and "flat" frequency response. More specifically, in terms of the American National Standards Institute Specification of Hearing Aid Characteristics (ANSI S3.22-1996), the device preferably has a peak saturated sound pressure level-90 ("SSPL90") equal to or below 110 decibels ("dB") and a high frequency average (HFA) SSPL90 will preferably not exceed 105 dB.

Figure 13:
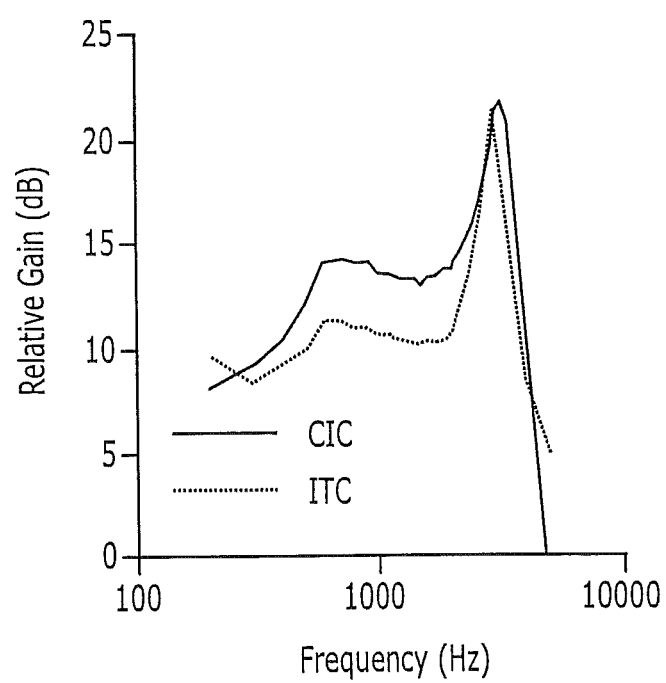
FIG. 13 is a graph of frequency (Hz) versus relative gain (dB) illustrating typical frequency responses of an ITC and CIC device with responses measured in HA1 and CIC couplers for the ITC and CIC devices, respectively.

In certain embodiments, a frequency response can be between at least 200-4000 Hz, and more preferably about 200-8000 Hz. In particular embodiments, the frequency response can be a "flat" in situ response with some compensatory gain between about 1000-4000 Hz. The high frequency average (i.e., 1000, 1600, and 2500) full-on gain is typically between 10-20 dB. For example, the compensatory gain can be about 10-20 dB between 1000-4000 Hz to accommodate for the loss of natural external ear resonance. This natural ear resonance is generally attributable to the occluding in the external auditory meatus and or concha when a CIC, ITE, ITC or ear mold from a BTE device is employed. The total harmonic distortion can be less than 10%, and typically less than about 1%. Maximum saturated sound pressure can be about 105 dB SPL with a high frequency average of 95-100 dB SPL and an equivalent input noise that is less than 35 dB, and typically less than 30 dB. FIG. 13 illustrates examples of typical coupler frequency responses for ITC and CIC devices (conventionally used for treating stuttering pathologies) with the graph illustrating examples of the frequency response curve of typical devices in a non-altered setting.

Figure 14:
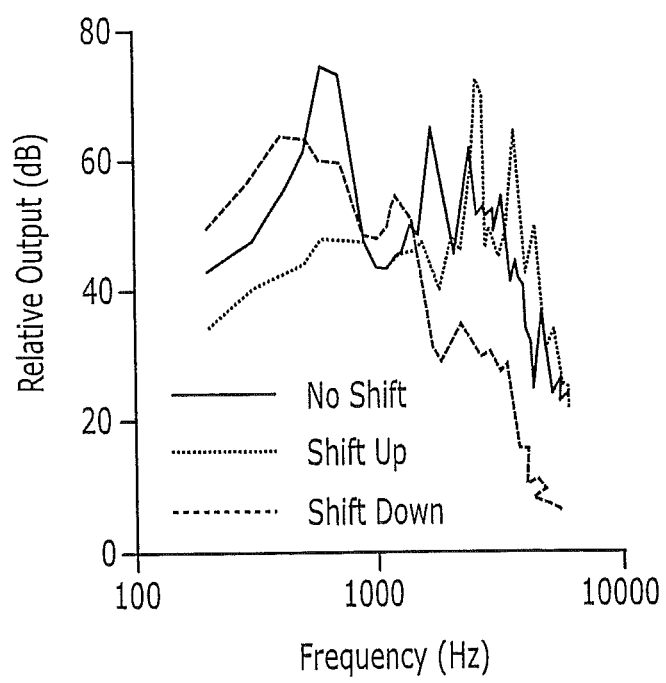
FIG. 14 is a graph of frequency (Hz) versus relative output (dB) illustrating typical frequency alterations in response to a synthetic vowel [ae] generated and delivered in sound field.

FIG. 14 illustrates frequency-altering capabilities of exemplary CIC configured devices. A synthetic vowel [ae] was generated and played in sound field to the device while coupler responses were recorded. Three recordings were made with each device: one with no alteration, one with maximum frequency shift up, and one with maximum frequency shift down. This experiment was originally primarily aimed to assess operational capability for stuttering pathologies, but clear shifts of the formant frequencies during frequency alterations relative to the nonaltered frequency response is evident. Similar results were obtained with an ITC model.

The invention will now be described in more detail in the following non-limiting examples.

EXAMPLES

Participants

The participants were 27 students, 15 normal reading sixth grade students and 12 sixth grade students diagnosed by their school as being reading delayed, attending local eastern North Carolina middle schools. The participants' overall reading ability score on the Woodcock Johnson Reading Mastery Test-Revised (WRMT-R) determined reading ability. Normal reading ability was defined as an age appropriate score. Delayed reading ability was defined as one or two years delayed relative to the age appropriate score. All participants had normal bilateral hearing sensitivity as determined by a screening protocol as well as normal or corrected vision as reported by their parents or school personnel. Passing scores for language screening (Clinical Evaluation of Language Functions-3) and average scores for receptive one-word picture vocabulary (Peabody Picture Vocabulary Test-III) were also required for participation.

Materials and Instrumentation

Research testing was conducted in a quiet room at the participant's middle school. For each experimental condition, the participants read three passages from the Formal Reading Inventory (Wiederholt, 1986), one reported to be at the third grade level, one at the sixth grade level, and one at the ninth grade level under both non-altered feedback (NAF) and frequency altered feedback (FAF). Following the reading of each passage, the participant then read and responded to five multiple-choice questions that assessed comprehension of the written material.

For the FAF condition, an audio-vocal closed-loop feedback device consisting of voice output from a microphone that was passed through a filter to produce the participant's voice, one-half octave above his normal speaking voice. The participant's voice was fed back to the participant without delay through a set of standard headphones.

Procedure

Participants were brought in to the testing room and administered the WRMT-R, Clinical Evaluation of Language Functions-3 Screening, and Peabody Picture Vocabulary Test-III. After a short break they returned to the testing room and the reading tasks and conditions were explained to them. For the altered feedback condition, the participant was asked to state his/her name, the school he/she attended, and count to 10. Conditions and tasks were randomized for the participants. The A and B forms of the Formal Reading Inventory were randomized between conditions for the participants so that some participants had Form A for Task 1 and others had Form B. The levels of the passages were also randomized with Third, Sixth, and Ninth Grade Passages occurring at different points during the testing. Tasks were counterbalanced across all participants. All of the reading tasks and conditions were audio-and video-taped for later scoring of decoding errors.

Measures

For the two auditory conditions, comprehension scores, and decoding errors were determined. Comprehension scores were based on the number correct for each passage with a perfect score being five. Two types of scores for the decoding errors were calculated: a total number of errors per passage and a total for each of the types of decoding errors for each passage. Reading decoding errors for each passage were coded as insertions/additions (insertion of a word or part of a sentence not in the original text), self corrections (correcting an error after an actual incorrect word has been used), omissions (leaving a word or words out of the passage), substitutions (using a word that either was semantically or functionally appropriate), part-word repetitions (the repetition of part of a word in the process of decoding it), or whole-word repetitions (repeating complete words before continuing to read the rest of the sentence).

Results

Figure 15:
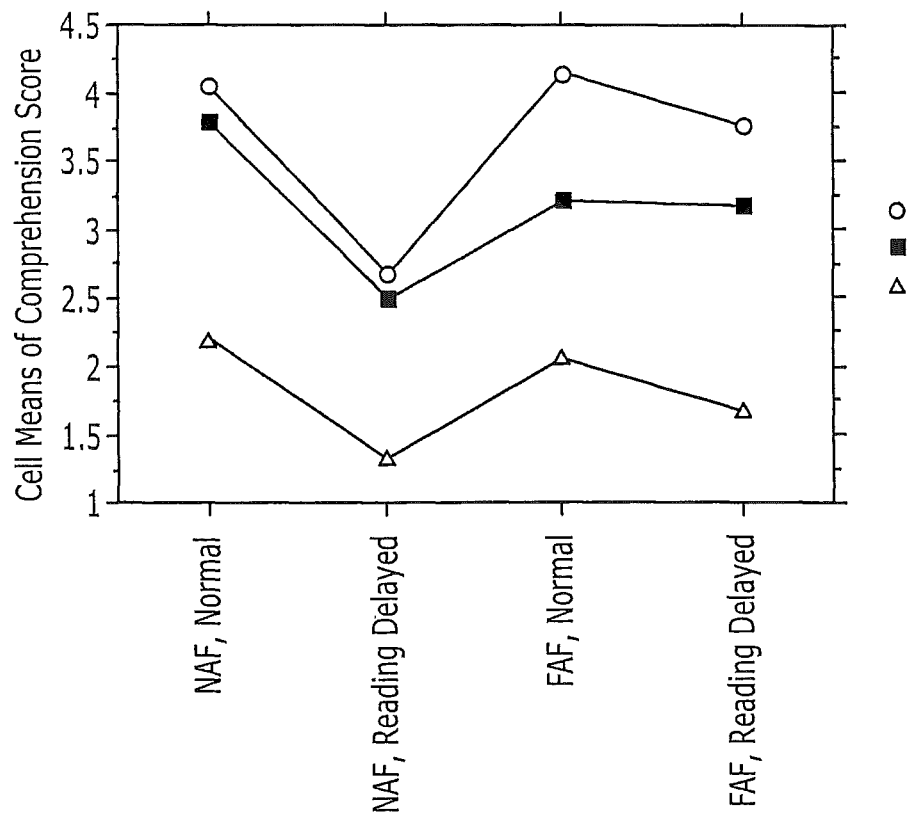
FIG. 15 is a graph of mean reading comprehension scores, as a function of group, reading level and auditory feedback according to embodiments of the present invention.
Figure 16:
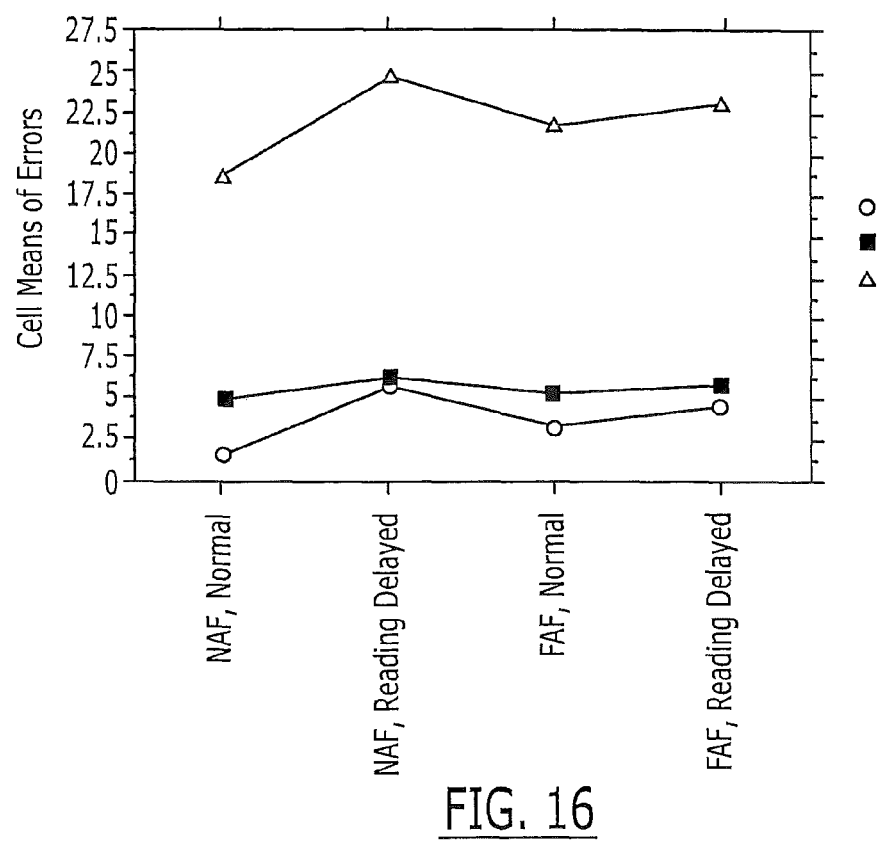
FIG. 16 is a graph of the mean number of reading errors as a function of group, reading level and auditory feedback.

Participants' mean comprehension scores, as a function of group, reading level and auditory feedback, are shown in FIG. 15. FIG. 16 depicts participants' mean reading errors as a function of group, reading level and auditory feedback.

Figure 17:
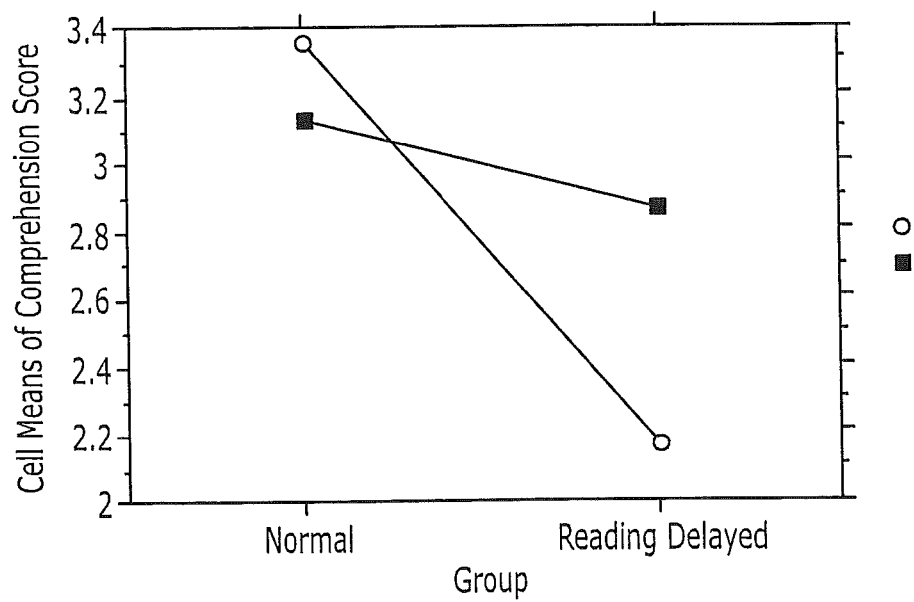
FIG. 17 is a graph of mean reading comprehension scores as a function of group and auditory feedback for normal and delayed reading level.

A three-factor mixed analysis of variance (ANOVA) was undertaken to investigate mean differences in total comprehension scores as a function of group, reading level, and auditory feedback. Significant main effects of group and level were found ($p=0.0007$ and $0.0001$, respectively). A significant feedback by group effect (see FIG. 17) was also found ($p=0.0030$). All other interactions were not significant ($p>0.05$). In general, as reading level increased comprehension decreased. The normal reading participants, as expected, had better comprehension than the reading delayed participants. Single degree of freedom contrasts were employed to investigate the significant auditory feedback by group interaction (see FIG. 17). The reading delayed participants had significantly higher comprehension with FAF ($p=0.0002$) while there was no difference between the normal reading participants in NAF versus FAF ($p=0.41$). The reading delayed participants had significantly lower comprehension than the normal reading participants in NAF ($p=0.0001$) while there was no difference between the groups in FAF ($p=0.18$).

Figure 18:
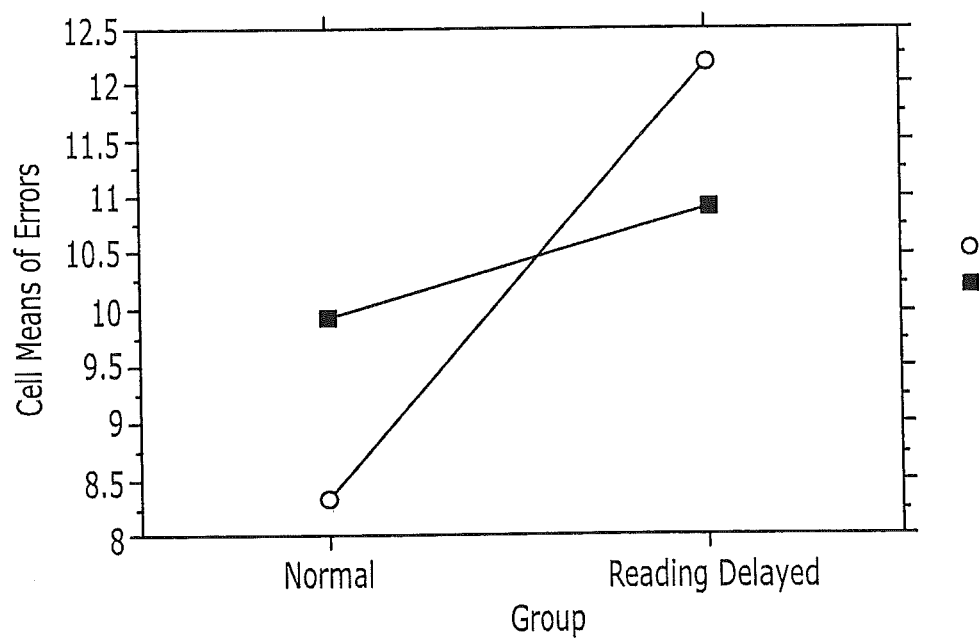
FIG. 18 is a graph of mean reading errors as a function of group and auditory feedback for normal and delayed reading level.

A three-factor mixed ANOVA was employed to investigate differences in mean reading errors as a function of group, reading level and auditory feedback. A significant main effect of level was found ($p=0.0001$). A significant auditory feedback by group effect (see FIG. 18) was also found ($p=0.0030$). All other main effects and interactions were not significant ($p>0.05$). In general, as reading level increased errors increased. Single degree of freedom contrasts were employed to investigate the significant feedback by group interaction (see FIG. 18). The reading delayed participants had significantly more errors with NAF versus FAF ($p=0.0007$) while there was no difference in errors with the normal reading participants in NAF versus FAF ($p=0.14$). The reading delayed participants had significantly more errors than the normal reading participants in NAF ($p=0.0095$) while there was no difference between the groups in FAF ($p=0.61$).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for improving reading comprehension of a subject, comprising:
    receiving an auditory speech signal of the subject at a first frequency;
    electronically altering the first frequency of the received auditory speech signal to generate a frequency altered feedback speech signal; and
    electronically administering the frequency altered feedback signal to the subject while the subject is speaking to improve the subject's reading comprehension.

2. A method according to claim 1, wherein the receiving step is carried out by electronically receiving an analog auditory speech signal at the first frequency, and wherein the electronically altering step comprises:
    electronically converting the received analog auditory speech signal to a digital signal in a frequency domain;
    electronically altering the frequency of the digital signal within a range of +/−2 octaves; then
    electronically converting the altered digital signal back to a time domain and into an analog signal to generate the frequency altered feedback signal that is administered to the subject.

3. A method according to claim 2, wherein at least one of the steps of converting the received analog signal, altering the digital signal, and converting the altered digital signal is at least partially carried out using circuitry in a remote device.

4. A method according to claim 2, wherein at least one of the steps of converting the received analog signal, altering the digital signal, and converting the altered digital signal is at least partially carried out using circuitry in a wireless device remote from the headset or earset.

5. A method according to claim 1, wherein the step of receiving is carried out using a headset or earset with a microphone worn by the subject, and wherein the frequency altered feedback signal is in a range of ¼ and ½ octave above or below a normal speaking voice of the subject.

6. A method according to claim 1, wherein at least one of the steps of converting the received analog signal, altering the digital signal, and converting the altered digital signal is at least partially carried out using circuitry in a wired device remote from the headset or earset.

7. A method according to claim 1, wherein the subject has reading disorder, and wherein the step of administering is carried out as a therapeutic treatment to improve the subject's reading comprehension.

8. A method according to claim 1, further comprising programmably adjusting a frequency shift for the step of electronically altering the first frequency of the received auditory speech signal to generate the frequency altered feedback speech signal using a computer interface.

9. A method according to claim 1, wherein the subject is a pre-school, primary school or high school age student.

10. A method according to claim 9, wherein the method is carried out in a school setting.

11. A method according to claim 1, wherein the subject is a college student.

12. A method according to claim 1, wherein the subject is an adult with a reading disorder.

13. The method of claim 1, further comprising providing a display with a user interface that graphically illustrates a frequency altered feedback (FAF) adjustment parameter that allows a user to adjust a frequency and/or associated octave shift of the frequency altered auditory feedback signal using the user interface.

14. A system for treating a reading disability to improve reading comprehension, comprising:
a headset or earset device with a microphone;
a portable device that cooperates with the headset or earset to generate a frequency altered auditory feedback (FAF) signal and transmit the FAF signal to a subject while the subject is reading aloud to improve the subject's reading comprehension; and
a computer interface with a display that communicates with the portable device that allows programmable selection and/or adjustment of the frequency altered auditory feedback signal.

15. The system of claim 14, wherein the system is configured to treat an adult with a reading disability to improve reading comprehension.

16. The system of claim 14, wherein the portable device is a remote device that is wired to the headset or earset to generate the frequency altered auditory feedback so that frequency is shifted a desired amount within a range of between +/−2 octaves.

17. The system of claim 16, wherein the FAF signal is generated without any programmably defined delay.

18. The system of claim 14, wherein the system is configured to treat a school age student with a reading disability to improve reading comprehension.

19. The system of claim 14, wherein the portable device is remote from the headset or earset and wirelessly communicates with the headset or earset to generate the frequency altered auditory feedback so that frequency is shifted a desired amount within a range of between +/−2 octaves.

20. The system of claim 19, wherein the FAF signal is generated without any programmably defined delay.

* * * * *

UNITED STATES PATENT AND TRADEMARK OFFICE
CERTIFICATE OF CORRECTION

| | | |
|---|---|---|
| PATENT NO. | : 9,005,107 B2 | |
| APPLICATION NO. | : 13/570380 | |
| DATED | : April 14, 2015 | |
| INVENTOR(S) | : Rastatter et al. | |

It is certified that error appears in the above-identified patent and that said Letters Patent is hereby corrected as shown below:

In the specification:
Column 13, Line 20:
 Please correct "an AID converter"
  to read -- an A/D converter --

Signed and Sealed this
Fifteenth Day of March, 2016

Michelle K. Lee
*Director of the United States Patent and Trademark Office*